(12) United States Patent
Han et al.

(10) Patent No.: US 10,537,226 B2
(45) Date of Patent: Jan. 21, 2020

(54) ROTATIONAL SCANNING ENDOSCOPE

(71) Applicants: California Institute of Technology, Pasadena, CA (US); City of Hope, Duarte, CA (US)

(72) Inventors: Chao Han, Pasadena, CA (US); Lily L Lai, Glendale, CA (US); Jiangtao Huangfu, Pasadena, CA (US); Changhuei Yang, Pasadena, CA (US)

(73) Assignees: California Institute of Technology, Pasadena, CA (US); City of Hope, Duarte, CA (US)

(*) Notice: Subject to any disclaimer, the term of this patent is extended or adjusted under 35 U.S.C. 154(b) by 258 days.

(21) Appl. No.: 14/580,074

(22) Filed: Dec. 22, 2014

(65) Prior Publication Data

US 2015/0173593 A1    Jun. 25, 2015

Related U.S. Application Data

(60) Provisional application No. 61/920,279, filed on Dec. 23, 2013, provisional application No. 62/086,534, filed on Dec. 2, 2014.

(51) Int. Cl.
| | |
|---|---|
| *A61B 1/00* | (2006.01) |
| *A61B 1/05* | (2006.01) |
| *A61B 1/07* | (2006.01) |
| *A61B 1/31* | (2006.01) |
| *A61B 1/06* | (2006.01) |
| *G02B 23/24* | (2006.01) |

(52) U.S. Cl.
CPC ...... *A61B 1/00096* (2013.01); *A61B 1/00172* (2013.01); *A61B 1/00177* (2013.01); *A61B 1/051* (2013.01); *A61B 1/0676* (2013.01); *A61B 1/0684* (2013.01); *A61B 1/07* (2013.01); *A61B 1/31* (2013.01); *G02B 23/2423* (2013.01); *G02B 23/2484* (2013.01); *A61B 1/00009* (2013.01); *A61B 1/0638* (2013.01)

(58) Field of Classification Search
CPC ... A61B 1/00096; A61B 1/00177; A61B 1/31; A61B 1/055
USPC ............................... 600/112, 122, 137, 142
See application file for complete search history.

(56) References Cited

U.S. PATENT DOCUMENTS

| 4,374,525 A * | 2/1983 | Baba ................... A61B 1/0052 600/146 |
|---|---|---|
| 4,375,818 A * | 3/1983 | Suwaki ............. A61B 1/00177 600/101 |
| 4,396,834 A * | 8/1983 | Appel .................. G03B 27/542 250/216 |

(Continued)

FOREIGN PATENT DOCUMENTS

| JP | 2010-012222 A | 1/2010 |
|---|---|---|
| WO | WO2015/100264 | 7/2015 |

OTHER PUBLICATIONS

International Search Report and Written Opinion dated Apr. 17, 2015 in PCT/US2014/071983.

(Continued)

*Primary Examiner* — Timothy J Neal
*Assistant Examiner* — Jae Woo
(74) *Attorney, Agent, or Firm* — Mintz Levin Cohn Ferris Glovsky and Popeo, P.C.

(57) ABSTRACT

A rotational scanning endoscope for rotationally scanning to capture a circumferential image

20 Claims, 21 Drawing Sheets

(56) References Cited

U.S. PATENT DOCUMENTS

| | | | | |
|---|---|---|---|---|
| 4,424,523 A * | 1/1984 | Snelling | H04N 1/024 | 347/130 |
| 4,471,384 A * | 9/1984 | Sato | H04N 1/0318 | 235/469 |
| 4,489,728 A * | 12/1984 | Matsuo | A61B 1/0052 | 600/146 |
| 4,615,330 A * | 10/1986 | Nagasaki | A61B 1/00177 | 128/901 |
| 5,430,475 A * | 7/1995 | Goto | H04N 7/18 | 348/65 |
| 5,649,897 A * | 7/1997 | Nakamura | A61B 1/05 | 348/45 |
| 5,699,102 A * | 12/1997 | Ng | H04N 1/4015 | 347/224 |
| 5,871,439 A * | 2/1999 | Takahashi | A61B 1/00059 | 348/74 |
| 5,898,510 A * | 4/1999 | Kaihotsu | H04N 1/484 | 358/505 |
| 6,490,083 B1 * | 12/2002 | McManus | A61B 1/3135 | 359/368 |
| 6,749,572 B2 * | 6/2004 | Edwardsen | A61B 1/00177 | 600/459 |
| 7,841,980 B2 * | 11/2010 | Minosawa | A61B 1/00177 | 600/103 |
| 7,896,803 B2 * | 3/2011 | Schara | A61B 1/00177 | 600/130 |
| 8,602,971 B2 * | 12/2013 | Farr | A61B 1/0607 | 600/109 |
| 9,894,329 B2 * | 2/2018 | Melville | A61B 1/0008 | |
| 9,974,430 B2 * | 5/2018 | Bandy | A61B 1/041 | |
| 2002/0109774 A1 * | 8/2002 | Meron | A61B 1/00096 | 348/74 |
| 2003/0125719 A1 * | 7/2003 | Furnish | A61B 1/00073 | 606/15 |
| 2003/0228553 A1 * | 12/2003 | Mandelkern | A61B 1/00016 | 433/29 |
| 2004/0076319 A1 * | 4/2004 | Fauver | G01N 15/1468 | 382/133 |
| 2004/0249247 A1 | 12/2004 | Iddan | | |
| 2005/0003323 A1 * | 1/2005 | Katsuda | A61B 1/00089 | 433/29 |
| 2005/0143644 A1 | 6/2005 | Gilad et al. | | |
| 2005/0143664 A1 * | 6/2005 | Chen | A61B 5/6852 | 600/478 |
| 2005/0234347 A1 * | 10/2005 | Yamataka | A61B 1/0008 | 600/476 |
| 2006/0072176 A1 * | 4/2006 | Silverstein | G06T 3/005 | 358/540 |
| 2008/0253724 A1 * | 10/2008 | Uchida | A61B 1/07 | 385/117 |
| 2009/0137876 A1 * | 5/2009 | Brophy | A61B 1/00177 | 600/167 |
| 2009/0316116 A1 * | 12/2009 | Melville | A61B 1/0008 | 353/31 |
| 2010/0016662 A1 * | 1/2010 | Salsman | A61B 1/00096 | 600/109 |
| 2010/0016673 A1 * | 1/2010 | Bandy | A61B 1/041 | 600/178 |
| 2010/0069747 A1 * | 3/2010 | Watanabe | A61B 5/0066 | 600/427 |
| 2010/0312057 A1 * | 12/2010 | Konno | A61B 1/00177 | 600/162 |
| 2010/0324373 A1 * | 12/2010 | Lei | A61B 1/00096 | 600/176 |
| 2011/0282166 A1 | 11/2011 | Chen et al. | | |
| 2011/0288374 A1 * | 11/2011 | Hadani | A61B 1/00177 | 600/113 |
| 2012/0196320 A1 * | 8/2012 | Seibel | G01N 1/30 | 435/40.52 |
| 2012/0232408 A1 * | 9/2012 | Weller-Brophy | A61B 1/00165 | 600/478 |
| 2013/0345510 A1 * | 12/2013 | Hadani | A61B 1/00183 | 600/113 |
| 2016/0153765 A1 * | 6/2016 | Yamazaki | A61B 5/0066 | 356/479 |
| 2016/0174813 A1 * | 6/2016 | Rose | A61B 1/00096 | 600/176 |
| 2016/0235305 A1 * | 8/2016 | Wang | A61B 5/0062 | |

OTHER PUBLICATIONS

Göröcs, Z. et al.,"Gigapixel fluorescent imaging over an ultra-large field-of-view using a flatbed scanner," Lab Chip 13, pp. 4460-4466 (2013).

Kumar B. et al., "The acetowhite test in genital human papillomavirus infection in men: what does it add?," J. Eur. Acad. Dermatol. 15, 27-29 (2001).

Zheng, G.A. et al., "0.5 gigapixel microscopy using a flatbed scanner," Biomed. Opt. Express 5, 1-8 (2014).

CIS Technology, Canon, Canon Components, Inc., Japanese, 2008, https://www.canon-compo.co.jp/e/technology/cis.html.

Johnson, L. G. et al., "Anal cancer incidence and survival: The surveillance, epidemiology, and end results experience, 1973-2000," Cancer 101, pp. 281-288 (2004).

Nelson, R. A. et al., "Changing Patterns of Anal Canal Carcinoma in the United States," J. Clin. Oncol. 31, pp. 1569-1575 (2013).

Frisch, M. et al., "Sexually transmitted infection as a cause of anal cancer," New Engl. J. Med. 337, pp. 1350-1358 (1997).

Pineda, C. E. et al., "High resolution anoscopy in the planned staged treatment of anal squamous intraepithelial lesions in HIV-negative patients," J. Gastrointest. Surg. 11, pp. 1410-1415 (2007).

Silva, I. et al., "High-resolution anoscopy in the diagnosis of anal cancer precursor lesions in renal graft recipients," Ann. Surg. Oncol. 15, pp. 1470-1475 (2008).

Jay, N., et al., "Colposcopic appearance of anal squamous intraepithelial lesions—Relationship to histopathology," Dis. Colon Rectum 40, pp. 919-928 (1997).

Wilkin, T.J., et al., "Anal intraepithelial neoplasia in heterosexual and homosexual HIV-positive men with access to antiretroviral therapy," J. Infect. Dis. 190, pp. 1685-1691 (2004).

Smith, W.J., "Modern Optical Engineering," McGraw-Hill, Inc. (2000), p. 281-287.

NSG America, Inc.,SELFOC Lens Arrays for Line Scanning Applications.

Van Wamelen, PB et al., "A fast expected time algorithm for the 2-D point pattern matching problem," Computational Geometry, (2002).

VITECH Products Stepping Motor. Vitai Technology Co., LTD. (2004) Web. May 31, 2018. 2 pages. http://www.vitech.com.tw/products/motors/04.html.

* cited by examiner

ROTATIONAL SCANNING ENDOSCOPE

CROSS-REFERENCES TO RELATED APPLICATIONS

This application is a non-provisional application of and claims benefit to U.S. Provisional Patent Application No. 61/920,279, titled "Portable And Low-Cost Anal Canal Scanner for Screening of Anal Cancer," filed on Dec. 23, 2013 and U.S. Provisional Patent Application No. 62/086,534, titled "Portable And Low-Cost Anal Canal Scanner for Screening of Anal Cancer," filed on Dec. 2, 2014, both of which are hereby incorporated by reference in their entirety and for all purposes.

BACKGROUND

Embodiments of the present invention generally relate to imaging devices and methods thereof. More specifically, certain embodiments pertain to rotational scanning endoscopes, rotational scanning endoscope systems, and rotational scanning endoscope methods. In certain embodiments, the rotational scanning endoscope may be a portable and/or low-cost anal canal scanner that can be used, for example, to screen for anal cancer.

Anal cancer is a malignancy of the epithelium of the anal canal. As a malignancy that is associated with human papilloma virus (HPV) infection, the incidence of anal canal cancer has increased markedly over the last two decades. Although screening for anal cancer results in early detection, screening of at-risk populations has not been widely adopted. The current gold standard for anal cancer screening is high resolution anoscopy, a technique adapted from standard cervical examination protocols. In brief, the procedure is conducted as follows: 3-5% acetic acid is applied using soaked gauze into the anal canal for at least one minute. The gauze is removed and a clear plastic anoscope is passed into the anal canal to retract soft tissues away and to allow the anal mucosa to be evaluated. The colposcope is positioned and used to identify abnormal areas delineated by acetic acid and labeled as "acetowhite" areas. These areas are biopsied to obtain a histological confirmation of the abnormality. A handwritten map and photographs of abnormal areas document the location, appearance, and clinical impression of the biopsied areas.

Although high resolution anoscopy is the current standard examination procedure used to screen for anal cancer, this technique has significant limitations. For example, a conventional colposcope (e.g. Olympus OCS-3) used in this procedure has an adjustable magnification in the range of 3×-17× with a field of view from 13-84 mm. The geometry of the anal canal only allows a conventional colposcope to view small areas of the anal canal at any given time. To complete the entire examination, this colposcope would have to be moved and refocused multiple times. In addition, the ability to identify abnormal tissue from the normal tissue is highly dependent on the skill level of the practitioner and the number of biopsies taken during examination. Moreover, the typical anoscopy exam procedure is charted manually. Also, digital photographs of areas of concern are highly desirable for serial follow-up but are logistically difficult to implement with the conventional procedures. Taken together, the entire conventional procedure is time consuming with an average of more than 30 minutes per exam, requires multiple steps in its set up and execution, depends on the skill set of the provider to identify abnormal areas requiring biopsies, and demands high levels of histopathologic resources for support. A simpler, cheaper, and better alternative for imaging the anal canal for screening purposes is needed.

BRIEF SUMMARY

Certain embodiments described herein generally relate to image scanning techniques. More specifically, certain aspects pertain to rotational scanning endoscopes, rotational scanning endoscope systems, and rotational scanning endoscope methods.

Certain embodiments pertain to a rotational scanning endoscope comprising a substantially transparent tube, a motor, and an imaging module. The substantially transparent tube is configured for insertion into a specimen. The motor is configured to rotate an axial member. The imaging module is mounted to the axial member located within the substantially transparent tube. The imaging module is configured to rotationally scan a circumferential surface outside the tube during a rotation of the axial member. In some cases, the imaging module comprises an illuminator, an imaging sensor, and a lens array (e.g., an array of SELFOC lenses). The illuminator is configured to provide illumination to a longitudinal segment of the specimen. The image sensor is configured to capture an image of the illuminated segment of the specimen at each sample time. The lens array is configured to project an image of the illuminated segment to the image sensor. In one case, the lens array is an array of cylindrical lenses, wherein the lens array and the image sensor are located such that the lens array projects a 1:1 image to the image sensor.

Certain embodiments pertain to a rotational scanning endoscope system comprising a tube, a motor, an imaging module, and one or more processors. The tube is configured for insertion into a specimen. The motor is configured to rotate an axial member. The imaging module is mounted to the axial member located within the tube. The imaging module is configured to rotationally scan a surface outside the tube during rotation of the axial member. The one or more processors are configured to generate an image of the specimen based on the rotational scan. In some cases, the imaging module comprises an illuminator, an image sensor, and an array of SELFOC lenses (SLA). The illuminator is configured to provide illumination to a longitudinal segment of the specimen. The image sensor is configured to capture an image of the illuminated segment of the specimen at each sample time. The SLA is configured to project an image of the illuminated segment to the image sensor. In one case, the SLA and the image sensor are located such that the SLA projects a 1:1 image to the image sensor.

These and other features are described in more detail below with reference to the associated drawings.

BRIEF DESCRIPTION OF THE DRAWINGS

FIG. 13B is a zoomed-in image of the rectangular region of the image in FIG. 13A.

FIG. 13C is a zoomed-in image of the rectangular region of the image in FIG. 13B.

DETAILED DESCRIPTION OF THE INVENTION

Certain embodiments described herein pertain to rotational scanning endoscopes, rotational scanning endoscope systems, and rotational scanning endoscope methods. A rotational scanning endoscope generally refers to an endoscopic device configured to be inserted into a specimen and that is able to rotationally scan with a wide field-of-view over a circumferential surface outside the device to capture a circumferential image of the specimen. For example, a rotational scanning endoscope may comprise a substantially cylindrical and transparent tube configured to be inserted into an anal canal or other cavity of a body. The rotational scanning endoscope further comprises an imaging module within the tube that rotationally scans a circumferential surface of the cavity outside the tube. In certain embodiments, this rotational scanning endoscope may be a portable and/or low-cost anal canal scanner that can be used, for example, to screen for anal cancer.

I. Rotational Scanning Endoscopes and Rotational Scanning Endoscope Systems

Figure 1:
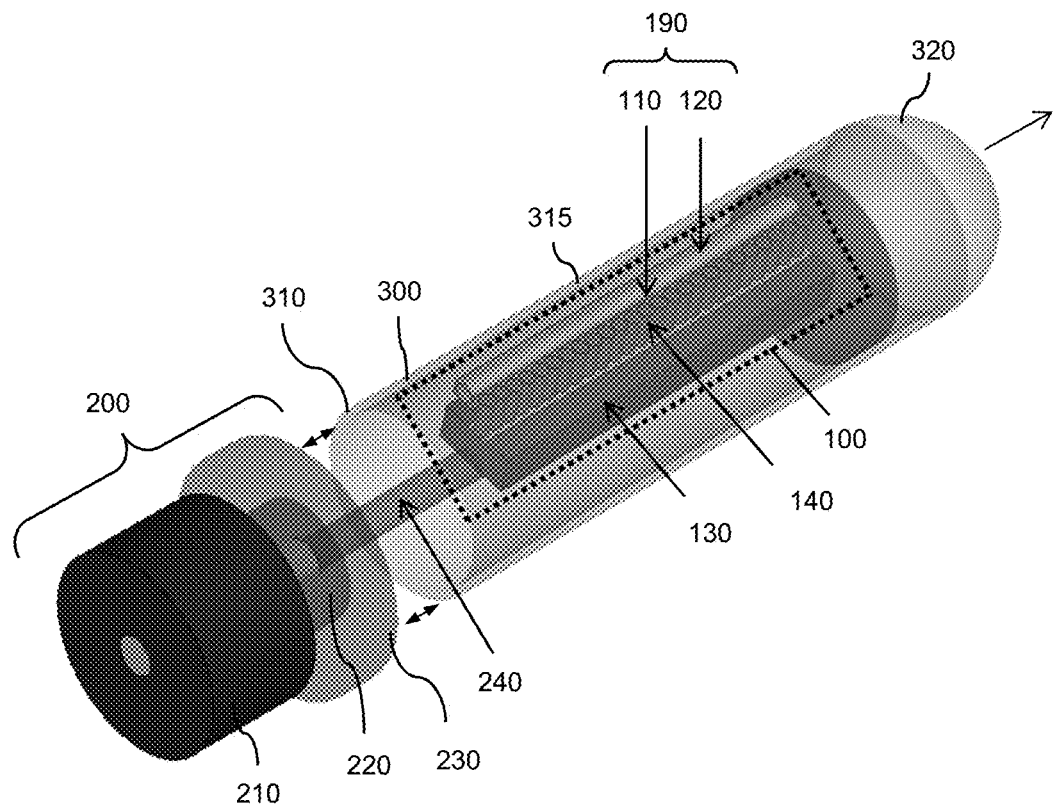
FIG. 1 is a schematic drawing of an isometric view of components of a rotational scanning endoscope, according to embodiments.

FIG. 1 is a schematic drawing of an isometric view of components of a rotational scanning endoscope 10, according to embodiments. This rotational scanning endoscope 10 comprises an imaging module 100, a motor assembly 200, and a substantially transparent tube 300 (e.g., polycarbonate tube). This rotational scanning endoscope 10 also comprises a longitudinal axis.

As used herein, an "imaging module" can refer to components of the rotational scanning endoscope within a tube. During image acquisition, the imaging module is rotated about a longitudinal axis to scan illumination to a circumferential surface (typically cylindrical at a constant radius from longitudinal axis) outside the tube. The imaging module captures raw image data that can be used to generate a circumferential image the illuminated surface. In most cases, the imaging module comprises an illuminator, a lens array (e.g., array of SELFOC lenses (SLA)), and an image sensor (e.g., CMOS image sensor). At each sample time, the components of the illuminator provide illumination to a longitudinal segment of the circumferential surface. As the imaging module is rotated, the illuminator scans this illumination across the circumferential surface of the specimen. The lens array projects the image of the illuminated segment to the image sensor. At each sample time, the image sensor captures a raw image of the illuminated segment. Generally the imaging module rotates about 360 degrees capturing multiple raw images that can be combined to capture a circumferential image of the circumferential surface. An example of certain components that can be included in an embodiment of the imaging module can be found at https://www.canon-compo.co.jp/e/technology/cis.html, which is hereby incorporated by reference for the description of LED Indirect Exposure configuration.

In the illustrated example shown in FIG. 1, the imaging module 100 comprises an illuminator 190, an image sensor 130, and a lens array 140 coupled to the image sensor. The illuminator 190 comprises a light emitter 110 and a light guide 120 coupled to the light emitter 110. In this example, the light emitter 110 includes a linear array of discrete light elements, each discrete light element including a red light-emitting diode (LED), a green LED, and a blue LED (together RGB LED) coupled to the light guide 120. The light guide 120 is configured to receive light from the light emitter 110 and provide uniform illumination to a longitudinal strip (segment) of the specimen corresponding to length of the light guide 120. The longitudinal strip is generally oriented in a direction parallel to the longitudinal axis. The lens array 140 is configured to project an image of the illuminated longitudinal strip of the specimen onto the image sensor 130. In this example, the lens array 140 is a linear collection of cylindrical lenses (e.g., SLA also called GRIN lenses) capable of 1:1 imaging (without magnification) onto the image sensor 130. A1

In FIG. 1, the motor assembly 200 comprises a motor 210, a gear 220, an adapter 230 coupling the motor 210 to the tube 300, and an axial member 240. The longitudinal axis of the rotational scanning endoscope 10 is at the centerline of the axial member 240 about which the axial member 240 can be rotated. The gear 220 is engaged between the motor 210 and the axial member 240. The axial member 240 is coupled at one end to the gear 220 for powering rotation of the axial member 240 by the motor 210 engaged with the gear 220. The imaging module 100 is mounted along the axial member 240. The substantially transparent tube 300 comprises a proximal end 310, central portion 315, and a distal end 320. In the illustrated example, the distal end 320 is rounded and the proximal end has an opening for receiving the adapter 230. Although not shown, the motor 210 and/or imaging module 100 may be in communication with a computing device (e.g., computing device 402 described with reference to FIG. 3) via wired or wireless connection.

In FIG. 1, arrows are shown to describe the motion of engagement and disengagement of the substantially transparent tube 300 to/from the rest of the rotational scanning endoscope 10. In this example, engagement of the substantially transparent tube 300 includes inserting the imaging module 100 into the substantially transparent tube 300 and coupling the substantially transparent tube 300 to the adapter 230. In one example operation, the substantially transparent tube 300 may be separated from the adapter 230 and discarded as disposable after acquiring the circumferential image.

In a typical image acquisition process, the imaging module (e.g., 100) within the substantially transparent tube (e.g., 300) is rotated about the longitudinal axis by about 360 degree to obtain an image of a circumferential surface of a specimen outside the substantially transparent tube. Usually control instructions are sent by a computing device (e.g., 400) to power the motor (e.g., 210) and engage a gear to rotate the axial member and the imaging module mounted thereon. In most embodiments, the motor rotates the axial member and the imaging module coupled thereon at a constant speed. In one example, the motor receives control instructions from a microcontroller and a motor control shield. During rotation of the imaging module, the light emitter (e.g., 110) provides illumination (e.g., RGB illumination) and a light guide (e.g., 120) channels uniform illumination to a longitudinal strip (i.e. strip parallel to direction of the longitudinal axis) along the circumferential cylindrical surface of the specimen outside the substantially transparent tube. Typically, the longitudinal segment is about the length of the light guide. A lens array (e.g., 140) receives light issuing from the illuminated specimen and projects an image of a longitudinal strip segment onto the surface of the image sensor (e.g., 130). At each sample time, the image sensor captures a raw image of the longitudinal segment of the specimen illuminated at that sample time. In many cases, the image sensor captures data based on three color channel illumination. The multiple raw images of longitudinal strip segments can be combined to generate the circumferential image.

In such a typical image acquisition process, illumination from the light emitter, the rotating speed of the motor, and the timing of images captured by the image sensor are controlled by instructions provided by a computing device (e.g., computing device 400 or 409). In one example, the illumination from the light emitter and the images captured by the image sensor are controlled by a circuit board and the software of a computing device such as described with respect to FIG. 9. In certain aspects, the rotating speed of the motor is calibrated to match the frame (sampling) rate of the image sensor. In these cases, the degree rotation of the imaging module between sampling times is sufficient to allow the image sensor to capture an image of a longitudinal segment that will be next to the previous image captured or overlap with the previous image captured (overlapping data). That is, the rotating speed of the motor and frame (sampling) rate of the image sensor will allow for capturing of images of longitudinal segments that are either next to each or overlap between adjacent longitudinal segments.

Although most embodiments of the acquisition process described herein involve a rotation of the imaging module of about 360 degrees, other rotations can be used to generate a partial circumferential image of the circumferential surface. For example, a 270 degree rotation may be used. As another example, a 180 degree rotation may be used. In addition, although the raw images and the circumferential image are described as RBG images in most embodiments, the images captured may be black and white images, or may be other color images.

Figure 2:
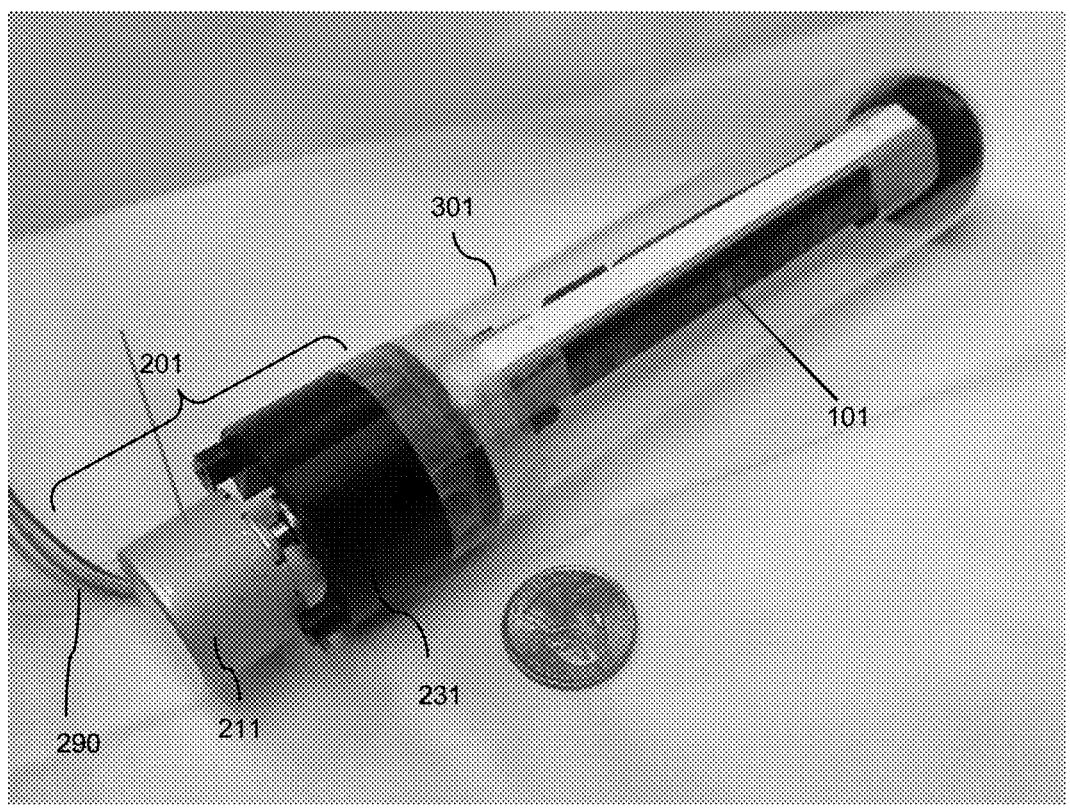
FIG. 2 is a photograph of a rotational scanning endoscope, according to an embodiment, and a quarter for scale.

FIG. 2 is a photograph of a rotational scanning endoscope 11, according to an embodiment. FIG. 2 also includes a photograph of a quarter beside the endoscope 11 for scale. As shown, the rotational scanning endoscope 11 is a portable, hand-held device. The illustrated rotational scanning endoscope 11 comprises an imaging module 101, a motor assembly 201 with a motor 211 and an adapter 231, and a substantially transparent tube 301. In FIG. 2, the rotational scanning endoscope 11 is shown with its adapter 231 engaged to the substantially transparent tube 301. The motor assembly 201 also includes wires 290 connected to the motor 211. These wires 290 may include power lines and/or communication lines for connecting to a computing device to receive control instructions and/or power for controlling the image acquisition process.

Figure 3:
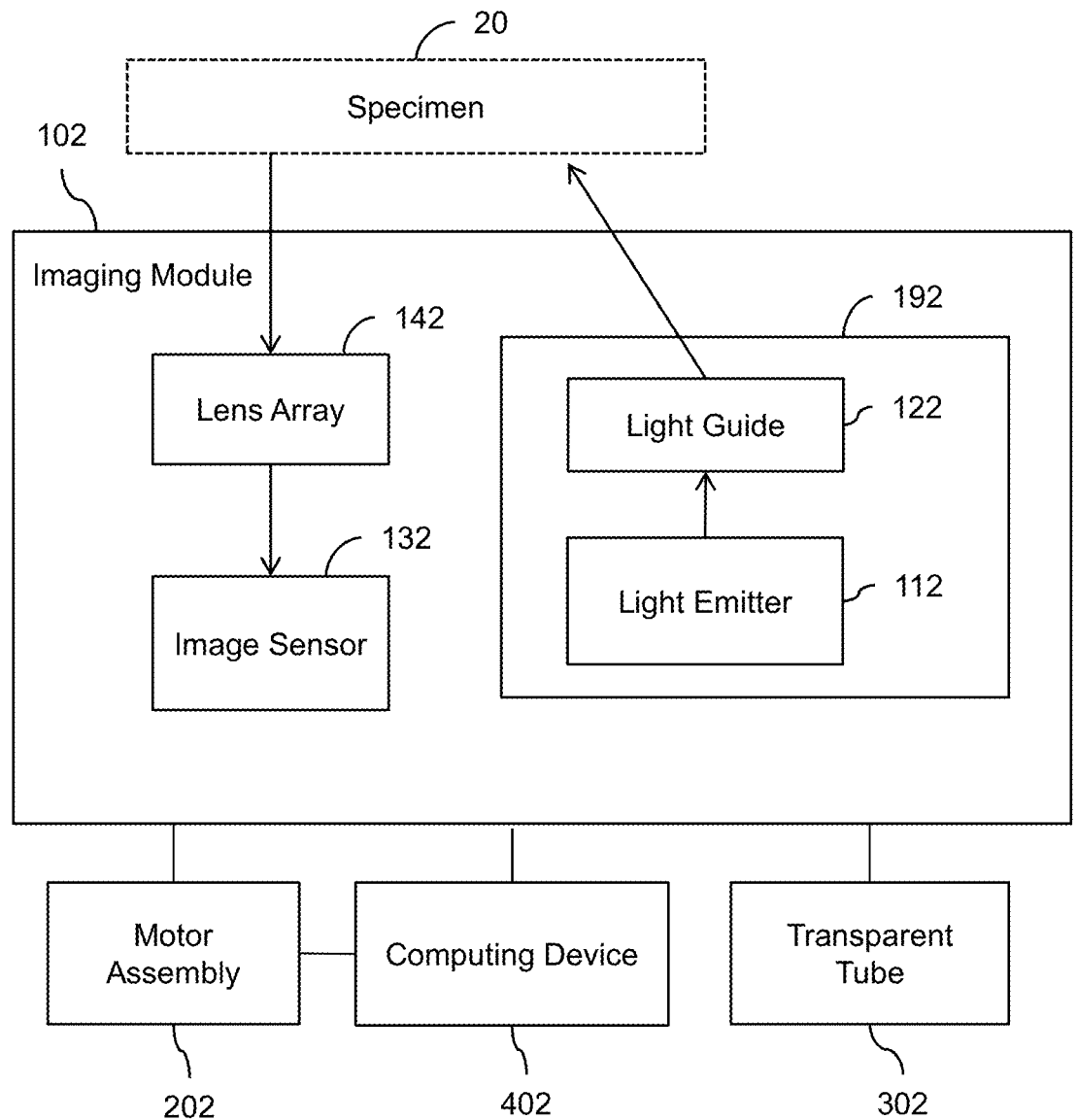
FIG. 3 is a schematic drawing of components of a rotational scanning endoscope system, according to embodiments.

FIG. 3 is a schematic diagram of components of a rotational scanning endoscope system 12, according to embodiments. The rotational scanning endoscope system 12 comprises a rotational scanning endoscope comprising an imaging module 102, a motor assembly 202, and a substantially transparent tube 302. The motor assembly 202 is coupled to the imaging module 102 to rotate the imaging module 102 during the image acquisition process. The substantially transparent tube 302 is coupled to the imaging module 102 to cover and/or otherwise protect the imaging module 102 during insertion into the specimen and during the image acquisition process. The rotational scanning endoscope system 12 also comprises a computing device 402 in communication with the imaging module 102 and the motor assembly 202 to communicate signals with control instructions to the motor assembly 202 and imaging module 102. Although not shown, the rotational scanning endoscope system 12 may also include a power supply in communication with the computing device 402. For illustration purposes, an optional (denoted by dashed line) specimen 20 is shown to illustrate certain interactions between components of the rotational scanning endoscope system 12 and the specimen 20.

In FIG. 3, the imaging module 102 comprises an illuminator 192, an image sensor 132, and a lens array 142 coupled to the image sensor 132. The illuminator 192 comprises a light emitter 112 and a light guide 122 coupled to the light emitter 112 to receive illumination from the light emitter 112. The light guide 122 provides uniform linear illumination to the specimen 20 generally along the length of the light guide 122. The lens array 142 receives light issuing from the illuminated specimen 20 and projects an image onto the surface of the image sensor 132. As the imaging module 102 is rotated, the image sensor 132 captures a circumferential image of a surface of the specimen 20 outside the transparent tube 302.

In certain embodiments, the imaging module comprises an illuminator configured to provide illumination at a sample time to a longitudinal strip along the circumferential surface. As the imaging module is rotated during an acquisition process, the illuminator scans illumination across the circumferential surface. The illuminator typically comprises a light emitter and a light guide coupled to the light emitter to channel illumination from the light emitter to the specimen.

The light emitter comprises one or more light sources. An example of a light source is an LED. Other light sources that may be used include a laser diode. The light sources may be visible light or infrared (IR) or ultraviolet (UV). In certain aspects, the light emitter comprises a plurality of discrete light elements which may be, for example, arranged in a one-dimensional array (e.g., linear or curvilinear array). In these cases, each discrete light element may comprise one or more individual light sources. For example, each discrete light element may comprise a red light source, a green light source, and a blue light source. In one such embodiment, each discrete light element comprises an RGE LED comprising a red LED, a LED, and a blue LED. An example of a light emitter in the form of a linear array of RGB LEDs is a RBG LED pipe.

The light guide comprises a plurality of discrete light guide elements. In some cases, the plurality of discrete light guide elements may be arranged in a one-dimensional array (e.g., linear or curvilinear array). In embodiments where the light emitter is a one-dimensional array of discrete light elements, the light guide may comprise a corresponding one dimensional array of light guide elements. In these cases, the discrete elements of the arrays may relate, for example, in one-to-one correspondence. As a group, the plurality of discrete light guide elements channels illumination from the light emitter to a longitudinal strip at the circumferential surface. In most cases, the longitudinal strip corresponds to the length of the light guide being illuminated. Although the light emitter and the light guide are described in many embodiments as a single one-dimensional array, these components may be multiple one-dimensional arrays or a two dimensional array in other embodiments. Each discrete light guide element comprises a first end proximal the light emitter, a second end opposing the first end, a light transmissive region between the first and second ends, and one or more inner surfaces forming a channel between the first and second ends. The channel may have any cross-sectional shape such circular, rectangular, etc. The inner surfaces are typically reflective surfaces of a reflective material and/or coated with a reflective material. The light guide elements are oriented in a direction normal to the circumferential surface being illuminated. For example, a light guide element may be in a substantially radial direction with respect to the substantially transparent tube.

Figure 4:
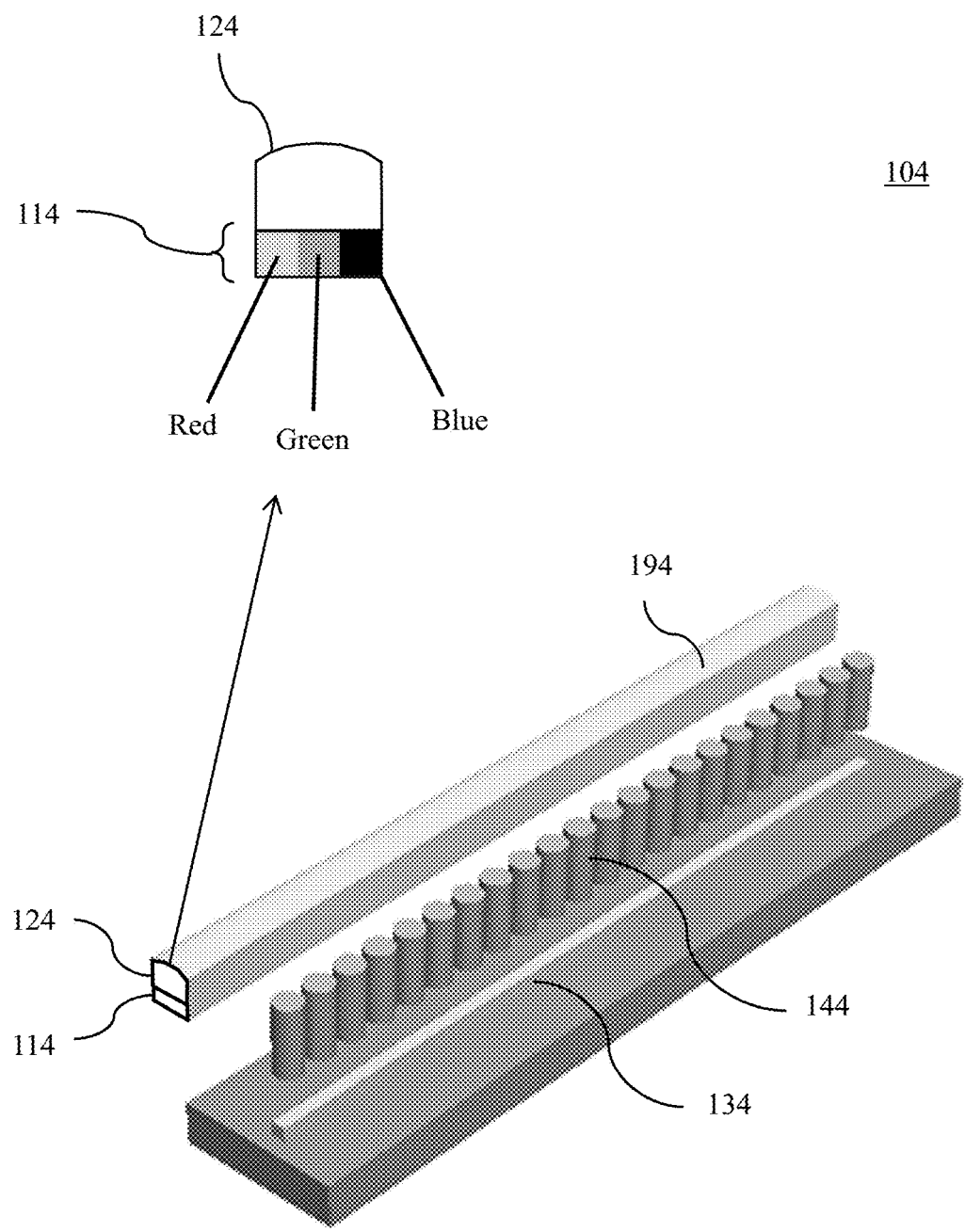
FIG. 4 is a schematic drawing of an imaging module comprising an illuminator, a lens array, and an image sensor, according to an embodiment.

FIG. 4 is a schematic drawing of an imaging module 104 comprising an illuminator 194, a lens array 144, and an image sensor 134, according to an embodiment. In this example, the illuminator 194 comprises a light emitter 114 and a light guide 124 coupled to the light emitter 114. The light emitter 114 is in the form of a one-dimensional array of discrete light elements, each discrete light element comprising three LEDs (red LED, green LED, and blue LED). The light guide 124 comprises a similar arrangement of discrete elements in a one-dimensional array of discrete light guides. In this example, each discrete light guide corresponds to a discrete light element, for example, in one-to-one correspondence. The light guide 124 is coupled to the light emitter 114 to receive light from the light emitter 114. The light guide 124 is directed to provide uniform illumination to a longitudinal strip of the specimen. The lens array 144 is coupled to the image sensor 134. The lens array 144 is configured to project an image of a longitudinal strip segment of the specimen onto the image sensor 134 at each sample time.

Figure 5:
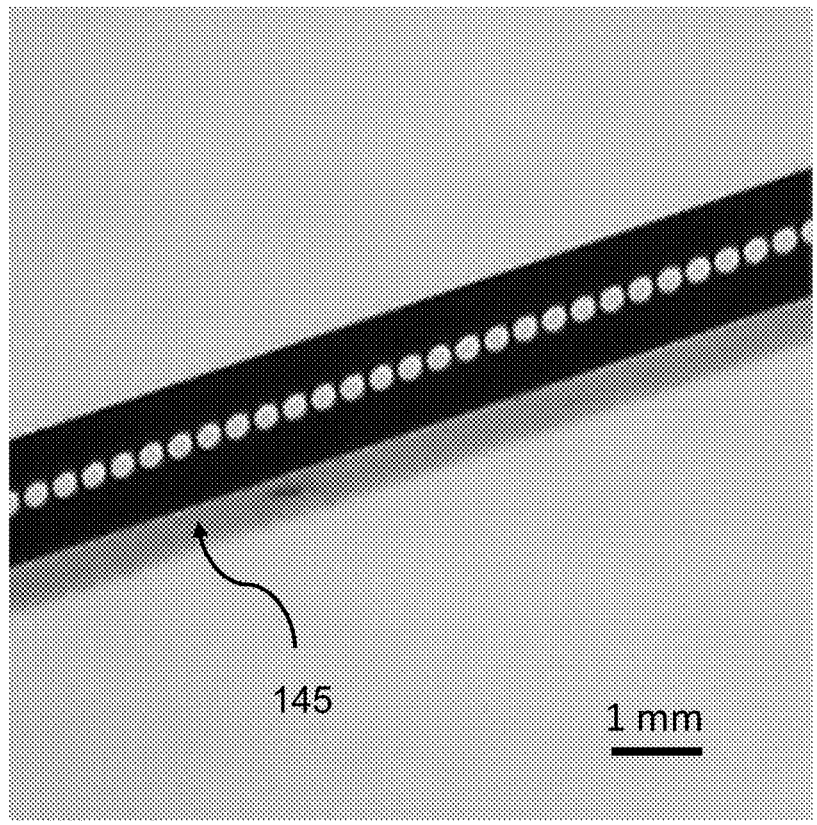
FIG. 5 is a photograph of a lens array that is a linear collection of SELFOC lenses (SLA), according to an embodiment.

In certain embodiments, the rotational scanning endoscope comprises a lens array that is designed to project an image of the illuminated longitudinal strip segment to the surface of the image sensor to be captured at each sample time. The lens array comprises a one-dimensional array (e.g., linear or curvilinear) of one or more lenses. In most cases, the lenses are cylindrical lenses such as SELFOC lenses also sometimes called GRIN lenses, and the like. In certain embodiments, the lens array is a linear collection of SELFOC lenses (SLA). SELFOC lenses and other cylindrical lenses are commercially available. The number of lenses in the lens array will depend on the total length of the lens array. In one embodiment, the number of lens in the lens array is in the range of 100-200. In another embodiment, the total length of the lens array is about 100 mm and the lens pitch is about 0.6 mm. In this case, the total number of lenses in the lens array is 100/0.6=167. In one embodiment, the number of lenses in the lens array is in a range of 100-200 lenses. In some cases, the lenses in the lens array may be coupled together in a linear arrangement for ease of assembly and alignment with the discrete sensor elements of the image sensor. Although many embodiments include a lens array that is a single one-dimensional array of lenses, other embodiments may include multiple one-dimensional arrays of lenses or a two-dimensional array of lenses. FIG. 5 is a photograph of an example of a lens array 145 in the form of an SLA.

In certain aspects, the lens array and image sensor may be configured to project a 1:1 image of the specimen onto the surface of the image sensor. In certain examples, the lens array may be comprised of cylindrical lenses to take advantage of their conjugate symmetry for 1:1 imaging. That is, under this conjugate symmetry, the working distance from the cylindrical lenses to the object being imaged ($L_O$) is identical to the working distance from the image sensor to the cylindrical lenses ($L_O$). Adding these two working distances (2L₀) to the lens length Z determines the Total Conjugate (TC) distance of the lens array: TC=Z+2L₀. The imaging module may be configured so that the surface of the image sensor is located at a distance of the Total Conjugate from about the outer surface of tube and the lens array may be located equidistance between the outer surface of the tube and the image sensor. By locating these components in this way, cylindrical lenses of the lens array with the will project a 1:1 image of the specimen onto the surface of the image sensor.

The image sensor may be a CMOS image sensor, a charge coupled device (CCD), an avalanche photo-diode (APD) array, a photo-diode (PD) array, a photomultiplier tube (PMT) array, or like device. These examples of image sensors and others are commercially available. In some cases, the image sensor may be an RGB image sensor. The image sensor comprises a plurality of discrete sensor elements, which may be in the arranged in the form of a one-dimensional array, multiple one-dimensional arrays, or a two-dimensional array. In many embodiments described herein, the image sensor is in the form of a one-dimensional array (e.g., linear or curvilinear) that matches or nearly aligns to the lens array so that each lens of the lens array may correspond to one or more discrete sensor elements of the image sensor. In one case, each lens uniquely corresponds to a sensor element in one-to-one correspondence. The discrete light detecting elements of the image sensor may have a size in the range of 1-10 microns. In one case, the discrete sensor element may have a size of about 1 micron. The discrete sensor elements may be circular, rectangular (e.g., square), or the like.

In embodiments where the lens array is an SLA, the refractive index of each SELFOC lens can be described as:

$$n(r)=n_0(1-kr^2/2) \quad \text{(Eqn. 1)}$$

Where: $n_0$ is the refractive index on the axis;
k is the gradient constant; and
r is the distance from the axis If the length of a SELFOC lens is Z, then its focal length f is given by:

$$f = \frac{1}{n_0\sqrt{k}\sin(Z\sqrt{k})} \quad \text{(Eqn. 2)}$$

The NA of a SELFOC lens can be expressed as f:

$$NA = n_0\sqrt{1-\text{sech}^2(D\sqrt{k})} \quad \text{(Eqn. 3)}$$

Where: D is the diameter of the SELFOC lens.

Equations 1-3 describing the working principle of a conventional SLA can be found in Smith, W. J., Modern Optical Engineering, McGraw-Hill, Inc., page 286 (2000), which is hereby incorporated by reference for this equation.

Some examples of properties of commercially available SLAs can be found in "SELFOC Lens Arrays for Line Scanning Applications," Intelligent Opto Sensor Designer's Notebook, p. 5, which is hereby incorporated by reference for these properties. An example of an SLA is a SLA-20D having properties of D=0.563 mm, Z=4.3 mm, L₀=2.4 mm, TC=9.1 mm, MTF (at 6 LP/mm, or 83 μm line-width)=60%, DOF=±0.3 mm. Some conventional SLAs have been used in contact image sensor systems such as flatbed scanners and business card scanners. In these systems, the SELFOC lens array is linearly translated along a flat surface of a document or the document is linearly translated across the SELFOC lens array to obtain a scanned image the document on a CMOS sensor. Some examples of contact image sensor systems can be found in Göröcs, Z., Ling, Y. Y., Yu, M. D., Karahalios, D., Mogharabi, K., Lu, K., Wei, Q. S., and Ozcan, A.,"Gigapixel fluorescent imaging over an ultra-large field-of-view using a flatbed scanner," Lab Chip 13, pp. 4460-4466 (2013) and Zheng, G. A., Ou, X. Z., Yang, C. H., "0.5 gigapixel microscopy using a flatbed scanner," Biomed. Opt. Express 5, 1-8 (2014), both of which are hereby incorporated by reference for the general concept of a SELFOC lens array.

Certain embodiments may provide one or more technical advantages. One advantage of embodiments is that the rotational scanning endoscope can image a circumferential surface within a cavity such as an anal canal. That is, the rotational scanning endoscope is configured to rotate the imaging module to capture an image. The components of the imaging module are also designed to mount to an axial member that is rotated by a motor. Moreover, the lenses and image sensor of imaging module are located at working distances to project an image of the specimen in a 1:1 imaging scheme to the image sensor. Another advantage of certain embodiments is that the rotational scanning endoscope may be configured to be a compact and portable rotational scanner endoscope for use in imaging internal cavities. In these cases, the components of the imaging module are specifically designed to fit within the geometry of a tube so that the rotational scanning endoscope can be inserted into the specimen and the imaging module within the tube rotationally scanned across a circumferential surface of the specimen outside the tube. In one case, the tube protecting the imaging module is designed to be detached and discarded after use. Another advantage of certain embodiments is that the rotational scanning endoscope provides wide field-of-view (e.g., of about 100 mm×120 mm) scanning of the specimen, which allows for fast and convenient imaging. This may be especially useful in regular screening of anal cancer. Another advantage may be that the rotational scanning endoscope may be fabricated with low cost and/or disposable components. An advantage a rotational scanning endoscope method may that it can complete a full scan of the entire circumferential surface in less than 10 seconds. In addition, images may be standardized and reproducible. Another advantage may be that using the rotational scanning endoscope does not require specialized training The overall imaging performance, the reproducibility of the images, and the ease-of use render may make this a highly attractive potential alternative to current imaging modalities of the anal canal and other cylindrically shaped anatomic sites, such as the esophagus.

Figure 6:
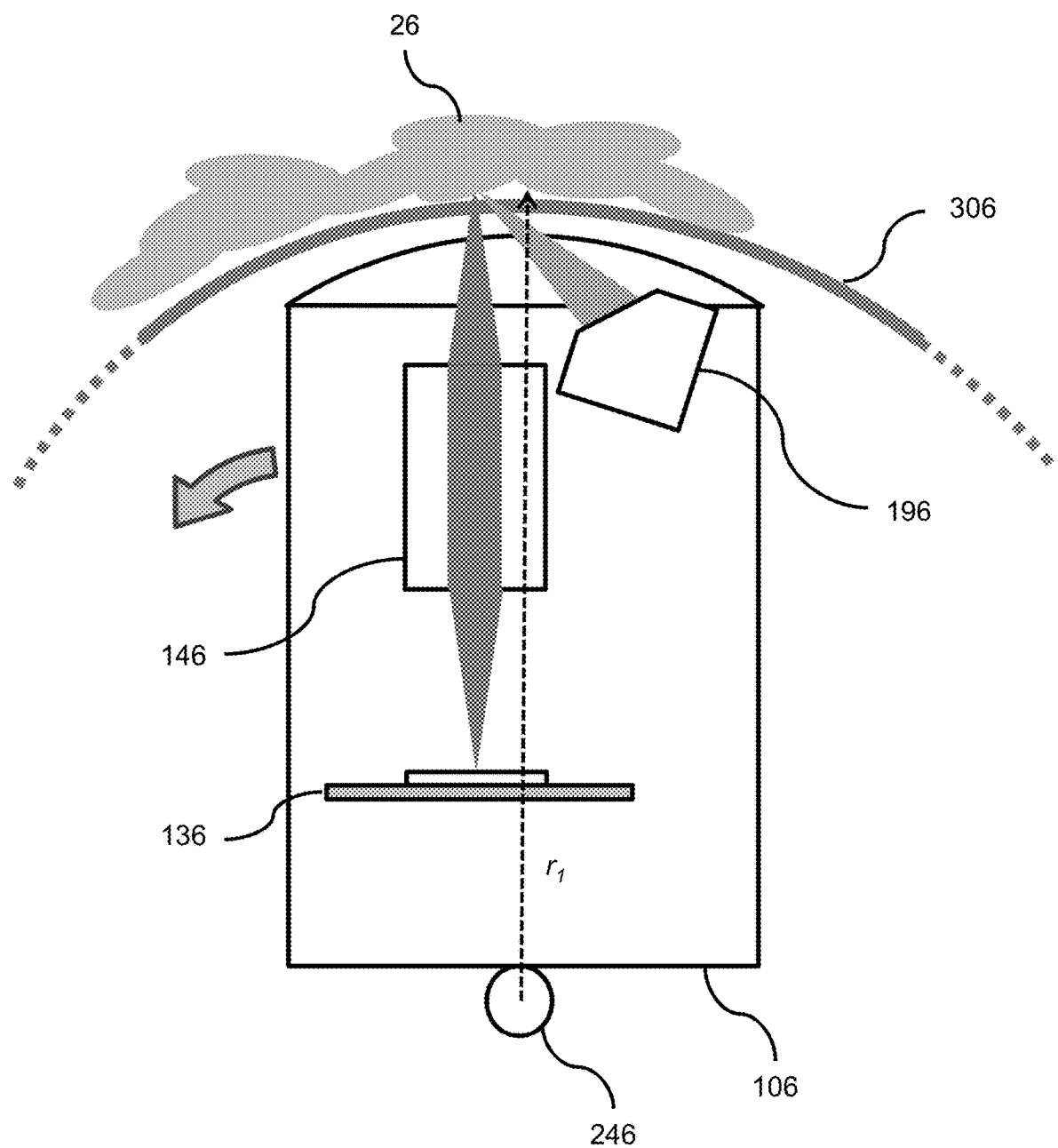
FIG. 6 is a schematic drawing of a partial cross-sectional view through a center portion of the tube of a rotational scanning endoscope during an image acquisition process, according to embodiments.

FIG. 6 is a schematic drawing of a partial cross-sectional view through a center portion of the tube of a rotational scanning endoscope during an image acquisition process for acquiring a circumferential image of a sample 26, according to embodiments. The cross-sectional view is normal to a longitudinal axis at the centerline of an axial member. The portion of the rotational scanning endoscope shown in FIG. 6 comprises an imaging module 106, a transparent tube 306, and an axial member 246. The imaging module 106 is shown being rotated in the counterclockwise direction (denoted by the arrow) about the centerline of the axial member 246 during the image acquisition process. FIG. 6 also illustrates a radius $r_1$ of the circumferential surface being imaged. The imaging module 106 comprises an illuminator 196, a lens array 146, and an image sensor 136. In this example, the lens array 146 is an SLA. To take advantage of the conjugate symmetry of the cylindrical lenses of the SLA, the image sensor 106 is located at a total conjugate distance from the cylindrical surface outside the transparent tube 306. The lens array 146 is located equidistance between the outer surface of the transparent tube 306 and the image sensor 136. By locating the components in this way, the SLA will project a 1:1 image of the specimen onto the surface of the image sensor.

In FIG. 6, the rotational scanning endoscope is shown at a sample time of the image sensor 136 during an image acquisition process for acquiring the circumferential image. At this time, the illuminator 196 is shown providing linear illumination to the specimen 26 along a longitudinal axis of the transparent tube 306 at the centerline of the axial member 246. Light issuing from the illuminated specimen 26 is received at the lens array 146. The illustrated light cone focused by the lens array 146 is perpendicular to the lens array 146, which is generally directed normal to the inner surface of the transparent tube 306. The lens array 146 projects an image to the image sensor 136. During a typical image acquisition process, the imaging module 106 is rotated at a constant speed inside the transparent tube 306. Generally, the imaging module 106 is rotated at least about 360 degrees (i.e., at least a circumferential scan) to be able to capture an image of the circumferential surface. During the rotation, line illumination from the illuminator 196 is rotationally scanned along the circumferential surface and the image sensor captures a circumferential image at the circumferential surface.

As used herein, a "tube" or "substantially transparent tube" can refer to a protective shell for the imaging module and other components of the rotational scanning endoscope during operation of the rotational scanning endoscope. At least the portions of the tube in the path of illumination between the imaging module and the specimen are made of a transparent material or substantially transparent material to allow the illumination to pass to the specimen and to receive light from the specimen. Some examples of such types of material include polycarbonate material, poly(methyl methacrylate) (PMMA), standard glass, Pyrex ®, or the like. In one example, the tube may be made of a Type 1, Class A glass material having a linear coefficient of expansion of 32-33×10-7 cm/cm° C.; annealing point of 560° C.±10° C.; softening point of 815-820° C.±10° C.; density, annealed of 2.23-2.24±0.01 g/cm³. In another example, the tube may be made of a Pyrex ® a linear coefficient of expansion of 32.5×10–7 cm/cm° C.; strain point of 510° C.; annealing point of 560° C.; softening point of 821° C.; density, annealed of 2.23 g/cm³; refractive index of 1.474 @ Sodium D line; temperature limits 490° C./230° C. (extreme service/normal service); and maximum thermal shock 160° C. The shape and material of the tube may be designed for insertion into the specimen, for receiving the imaging module, and/or for engaging and disengaging from the rest of the rotational scanning endoscope. In most cases, the tube has a generally cylindrically shape in the center portion and is generally hollow for receiving the imaging module. Other suitable shapes may be used. In certain aspects, the tube of the rotational scanning endoscope comprises a proximal end, a center portion, and a distal end. In certain cases, the proximal end may be configured to receive and/or engage with an adapter of the motor assembly. For example, the proximal end may have an opening (e.g., circular opening) that can receive the adapter. Correspondingly, the outer surface of the adapter be sized and shaped to fit within the tube and couple to the inner surface of tube to engage the tube to the adapter.

The center portion of the tube is configured to receive the imaging module. Generally, the center portion is substantially hollow and substantially transparent. In many cases, the center portion of the tube has a hollow cylindrical shape. The distal end may be rounded or have another shape that facilitates insertion into the specimen. In certain cases, the tube may have a size that is designed for receiving the imaging module and for ease of operation. In one example, the center portion has an inner diameter of 34 mm, an outer diameter of about 38 mm, and a length of about 145 mm.

In certain aspects, the tube may be a disposable component. For example, the tube may be used in in an image acquisition process and then separated from the rest of the rotational scanning endoscope and discarded.

Figure 7A:
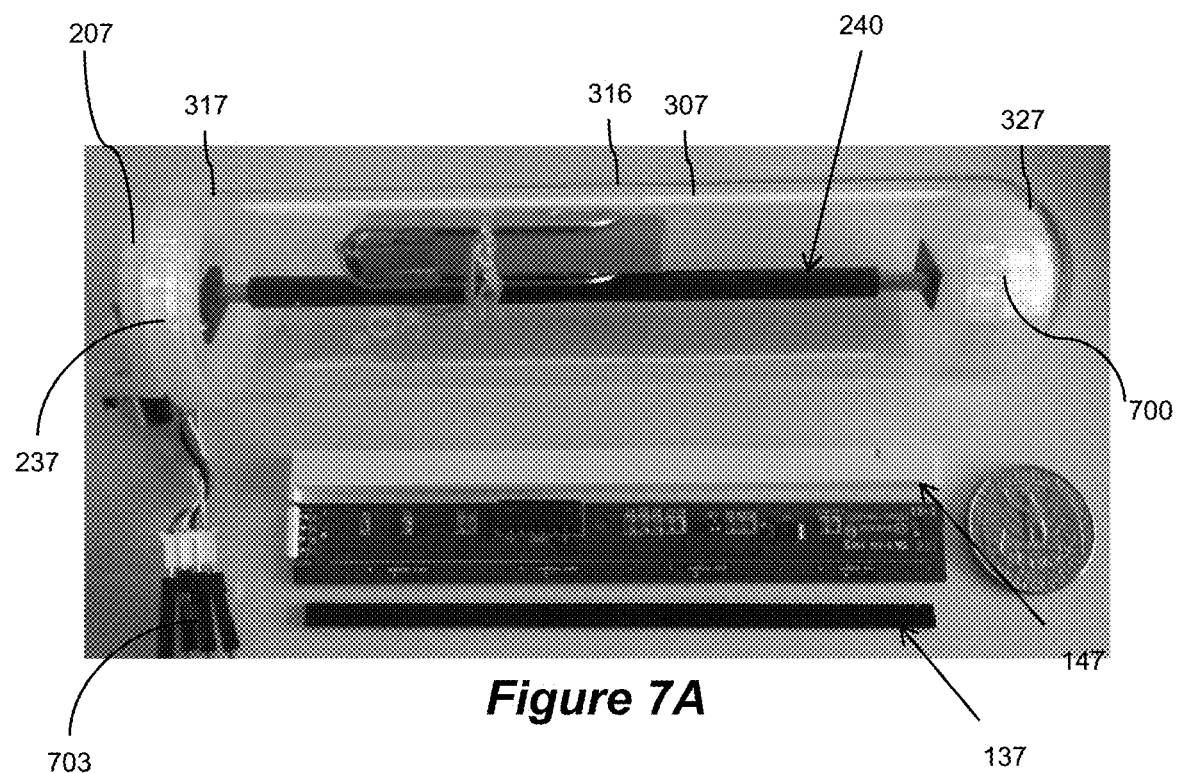
FIG. 7A is a photograph of some components of a rotational scanning endoscope, according to an embodiment.

FIG. 7A is a photograph of some assembled and some disassembled components of a rotational scanning endoscope, according to an embodiment. FIG. 7A also includes a photograph of quarter for scale. The illustrated components comprise a transparent tube 307 having a substantially cylindrical shape and a motor assembly 207 with an adapter 237 engaged to the transparent tube 307. The motor assembly 207 also comprises an axial member 240 having a first end and a second end. The first end is coupled to the motor assembly 207 to power rotation of the axial member 240. The tube 307 comprises a proximal end 317, a center portion 316, and a rounded distal end 327. The rotational scanning endoscope also includes an end receiving portion 700 coupled within the rounded distal end 327 of the tube 307. The end receiving portion 700 includes a center pivot member for receiving the second end of the axial member 240. The center pivot member can allow rotation and resist axial translational movement of the axial member 240. The end portion may be a molded piece that is attached to the inner surface of the hollow. The proximal end 317 of the transparent tube 307 is shown engaged to the adapter 237. FIG. 7A shows certain components arranged separately from the transparent tube 307 including a lens array 147 and an image sensor 137, according to an embodiment. The image sensor 137 comprises a linear strip of sensor elements in one to one correspondence with the lenses of the lens array 147. The rotational scanning endoscope includes wires 703 coupled to the motor assembly and/or for communication to the imaging module once assembled within the tube 307.

Figure 7B:
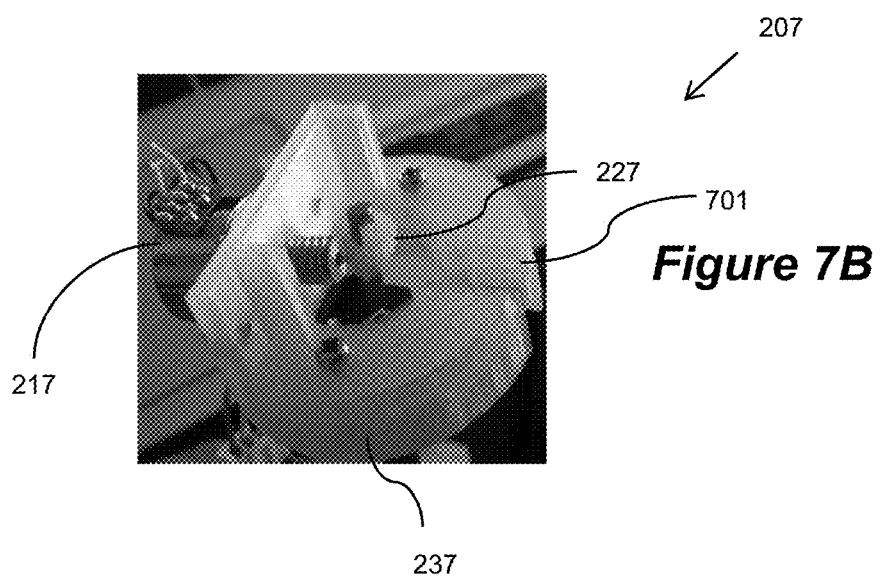
FIG. 7B is a zoomed in photograph of components of the motor assembly shown in FIG. 7A.

FIG. 7B is a zoomed in photograph of components of the motor assembly 207 shown in FIG. 7A. These components comprise an adapter 237, a motor 217 for powering the rotation of the axial member 240, and a worm gear 227 for coupling rotational motion from the motor 217 to rotation of the axial member 240. The adapter 237 has a cylindrical portion 701 for engaging with the proximal end 317 of the substantially transparent tube 307. In this example, the cylindrical portion 701 of the adapter 237 comprises an inset portion sized with a diameter that fits within the inner surface diameter of the tube substantially transparent 307. The cylindrical portion 701 comprises a portion with a larger sized diameter forming a stop to abut the edge of the substantially transparent tube 307.

In certain embodiments, the rotational scanning endoscope comprises a motor assembly configured for rotating the imaging module while within the transparent tube. The motor assembly comprises one or more of a motor, a gear(s), an adapter, and an axial member. The motor is designed to drive rotation of the axial member with an imaging module attached thereon. In some cases, the motor may be a geared stepper motor that includes the gear such as, for example, the 28 ByJ-48 by Kootek®. The gear(s) is coupled between the motor and the axial member to transition (e.g., step down)

the power between the motor and the axial member. The gear(s) is designed to transition the power from the motor to the axial member. The gear(s) may also transition rotation of the motor in one direction to rotation of the axial member in another direction such as shown in FIG. 7B. The axial member has a first end and a second end. The first end is coupled to the gear(s). In one case, the second end rotates within a fitting affixed within the distal end of the tube to prevent translation in the axial direction of the axial member. In certain cases, the axial member may be centrally located within the tube and/or oriented in a direction at the centerline of the tube.

In image acquisition processes of some embodiments, the motor rotates the axial member and imaging module coupled thereto to capture a circumferential image. During these processes, the motor generally rotates at a constant speed. In one case, the constant speed of the motor is about 8 mm/s. A longitudinal axis of the rotational scanning endoscope lies along a centerline of the axial member about which the axial member rotates. The radius of the circumferential surface being imaged is defined by the distance to the longitudinal axis. Generally the radius of the circumferential surface is at least the distance between the centerline of the axial member and the outer surface of the tube so that the circumferential surface is outside the tube.

In certain aspects, the rotational scanning endoscope comprises an adapter designed to provide connectivity between one or more of the motor, gear, axial member, and the substantially transparent tube. In some cases, the adapter has a first portion that can connect and allow motion of the motor, gear and axial member and a second portion for engaging (and sometimes disengaging) with the substantially transparent tube. For example, the adapter shown in FIG. 7B has a cylindrical portion 701 for engaging with the proximal end 317 of the tube 307. In this example, the cylindrical portion 701 of the adapter 237 comprises an inset portion sized with a diameter that fits within the inner surface diameter of the tube substantially transparent 307. The cylindrical portion 701 comprises a portion with a larger sized diameter forming a stop to abut the edge of the substantially transparent tube 307. In some cases, the adapter may include a separate tip placed into the distal end of the tube to receive the second end of the axial member. In one embodiment, the adapter is made of polyactide (PLA) material and fabricated by a 3D printer (e.g., MakerBot® Replicator 2 3D printer).

In one embodiment, the motor of a rotational scanning endoscope is of a two-piece configuration. An example of such a motor can be found at http://www.vitech.com.tw/products_motors_04.html, which is hereby incorporated by reference for this description of the motor.

In embodiments, the computing system provides control instructions to the motor and/or the imaging module of the rotational scanning endoscope to control the image acquisition process. In one such case, power to the motor and/or imaging module may be controlled by the computing device(s).

In certain embodiments, the computing device comprises a processor and a computer readable medium (CRM) in communication with the processor(s). In some cases, there may be processors in other components (e.g., motor, the image sensor, and the illuminator), which may receive and execute control instructions from the computing device. Optionally, the computing device may also comprise a display in communication with the processor. The processor is in electronic communication with CRM (e.g., memory) to receive signals with data such as image data in order to store/retrieve image data to/from the CRM. The processor is in electronic communication with the display to send image data and instructions to display images and other output to, for example, a user of the rotational scanning endoscope. The processor is also in electronic communication with the image sensor to send control instructions to the image processor and to receive signals with image data corresponding to the circumferential image acquired during each acquisition procedure. The processor is also in electronic communication with the light emitter to send control instructions to the light emitter to trigger illumination during an image acquisition procedure. The electronic communication between components of rotational scanning endoscope system and other systems and devices described herein may be in wired or wireless form. Generally the processor retrieves control instructions stored on the CRM and executes these control instructions to perform one or more functions of the rotational scanning endoscope system. For example, the processor may execute instructions stored on the CRM to perform one or more of the following functions: 1) interpreting image data of raw images of longitudinal segments captured by the image sensor at different sample times as the illuminator rotationally scans over the circumferential surface; 2) compiling a circumferential image of the specimen from the raw images; and 3) displaying a circumferential image on the display. The CRM can store instructions for performing certain functions of the rotational scanning endoscope system. These instructions are executable by the processor or other processing components of the system. The CRM can also store the images of the segments and other data generated by the system. Optionally, the rotational scanning endoscope system may include a display in electronic communication with the processor to receive image display data and display the circumferential image to the display. The display may be a color display or a black and white display.

Figure 8:
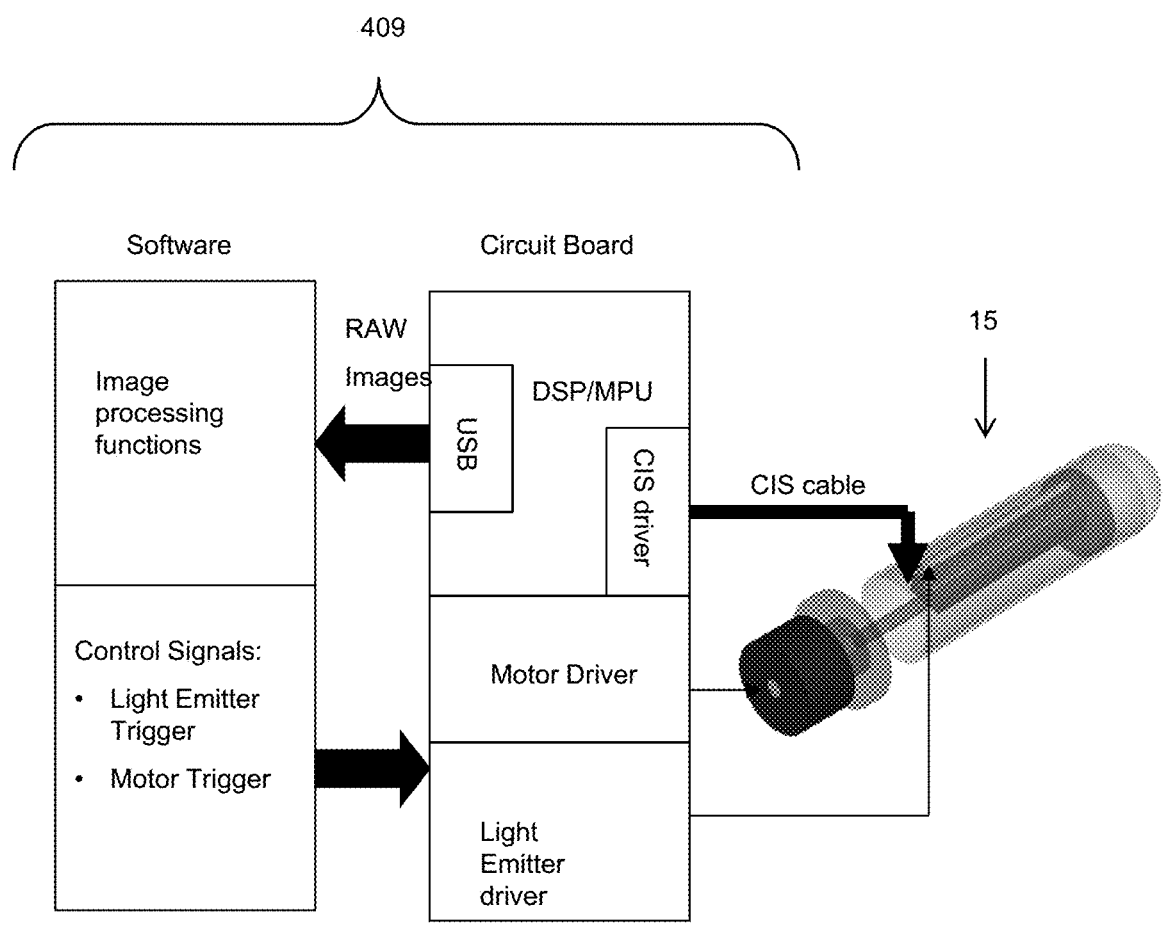
FIG. 8 is a schematic illustration of rotational scanning endoscope system comprising a rotational scanning endoscope and components of a computing device, according to an embodiment.

FIG. 8 is a schematic illustration of rotational scanning endoscope system 14 comprising a rotational scanning endoscope 15 and components of a computing device 409, according to an embodiment. The rotational scanning endoscope 15 comprises an imaging module comprising an illuminator, a lens array in form of an SLA, and an image sensor in the form of a CMOS sensor. In one example, the size of each of the sensor elements (pixels) in the CMOS image sensor is 42.3 µm. The rotational scanning endoscope 15 further comprises a motor assembly and a transparent tube. The components are similar in most respects to those of FIG. 1. The imaging module is mounted onto an axial member. The axial member was connected to a stepper motor with a gear. The mounted imaging module was inserted into a transparent tube. In this case, in the form of a glass tissue culture tube. The computing device 409 comprises a circuit board and a CRM for storing software. The software comprises imaging processing functions for interpreting raw images and processing these raw images to generate a circumferential image of the specimen. The software also comprises control instructions. The control instructions include light emitter trigger instructions for controlling the light emitter functions (e.g., intensity, illumination timing, intensity of illumination, etc.) and motor trigger instructions for controlling the motor functions (e.g., rotation speed, turning on and off, etc.). The circuit board comprises a DSP/MPU processor, a motor driver, and a light emitter driver. The circuit board further comprises a CIS driver in communication with the DSP/MPU processor. The CIS driver is configured to connect with a CIS cable for electrically connecting to the image sensor to receive raw image data. The circuit board further comprises a USB port in communication with the DSP/MPU processor. The USB port is configured to receive a USB connector connected to a line. The USB line is for electrically connecting to the CRM to receive signals with raw images (e.g., TIFF images) by the CRM. This USB line or another communication line may be used to send control signals to the motor driver and light emitter driver. The motor driver is in electrical communication with the motor for sending control signals with motor trigger functions. The light emitter driver is in electrical communication with the light emitter for sending control signals with light emitter trigger functions.

During an imaging acquisition process of the rotational scanning endoscope system 14 of FIG. 8, raw images of illuminated segments of the specimen are captured at sample times by the CMOS image sensor. Illumination from the light emitter and images capturing by the image sensor are generally controlled by the circuit board and software of the computing device 409. The stepper motor was controlled by a microcontroller plus a motor control shield. The rotating speed of the motor was calibrated to match the frame rate of the image sensor.

In some cases, the specimen being imaged by the rotational scanning endoscope may be a canal or other cavity of a body such as an anal canal, rectum, or esophagus. In these cases, the tube of the rotational scanning endoscope may be inserted through an opening of the canal or other cavity to position it to scan the circumferential surface of the canal or other cavity around the tube. Some illustrated examples of operating the rotational scanning endoscope to scan an anal canal of an animal are shown, for example, in FIG. 13A. In these examples, the distal rounded end of the tube is inserted into the anus of the animal. During the image acquisition process, the inside of the rectum and the anal canal of the colon can be imaged.

In one embodiment, an image acquisition process used RGB illumination to generate a RGB circumferential image by rotating the imaging module by 360°. The outer diameter of the surface being imaged was 4 cm and the total longitudinal length of the surface was 10.5 cm. The total scan time for this process was 15 seconds. The frame (sampling) rate of the image sensor was 200 fps. In this exemplary process, and RBG image of 600 dpi (42 µm pixel) was generated.

In one embodiment, the rotational scanning endoscope may comprise components that bend and/or flex during insertion into the specimen. For example, the tube may be flexible tubing. The imaging module may also be designed with components that are able to flex as the tube flexes.

II. Characteristics of an Embodiment of a Rotational Scanning Endoscope System

1. Resolution

The image resolution acquired in an exemplary operation of the rotational scanning endoscope system 14 described with respect to FIG. 8 is determined and discussed in this Section. In this embodiment, the image sensor used had a pixel pitch of 42.3 µm (600 dpi). To determine resolution of the images acquired by this system, groups 0-3 of the 1951 USAF resolution target were printed on a transparency film and the transparency film was attached to the outer surface of the cylindrical center portion of the tube of the rotational scanning endoscope 15 shown in FIG. 8. A typical acquisition process was completed rotating the imaging module about 360 degrees at a constant speed of 0.68 rad/sec. The illustration includes an x-axis and a y-axis on the transparency. The scan of the transparency was performed in the y-direction along the y-axis such that a longitudinal segment in the direction of the x-axis was imaged at each sample time during the acquisition process.

Figure 9A:
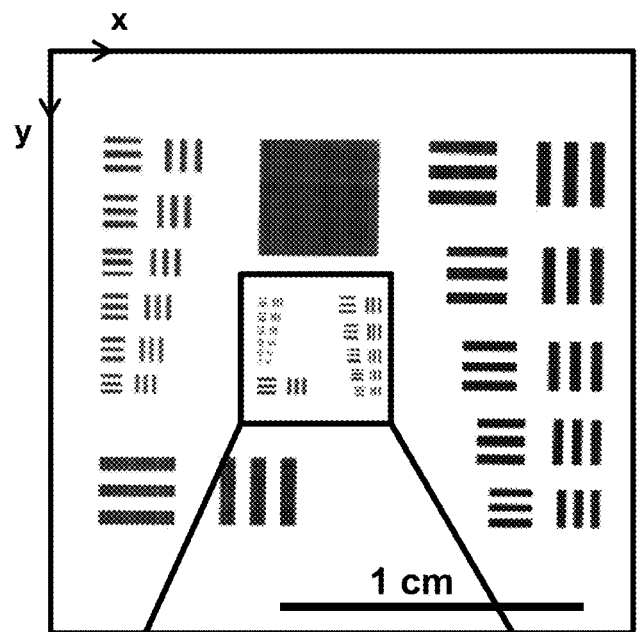
FIG. 9A is a circumferential image captured of the transparency during the image acquisition process, according to an embodiment.
Figure 9B:
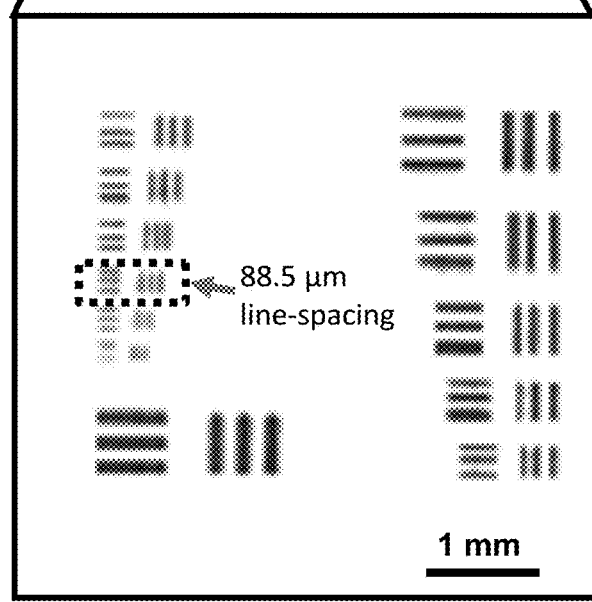
FIG. 9B is a zoomed-in rectangular region of the image shown in FIG. 9A.
Figure 9C:
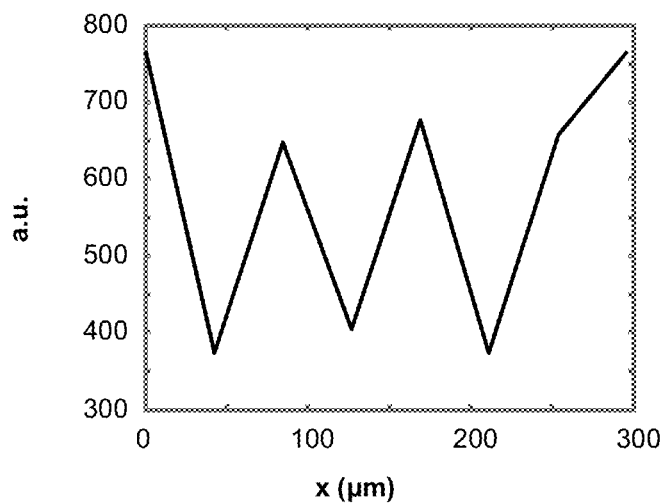
FIG. 9C are intensity profiles of the 11.3 line pairs per mm (lp/mm) element in the x(c) and y(d) directions after summing the red, green, and blue (RBG) channels, according to an embodiment.
Figure 9C:
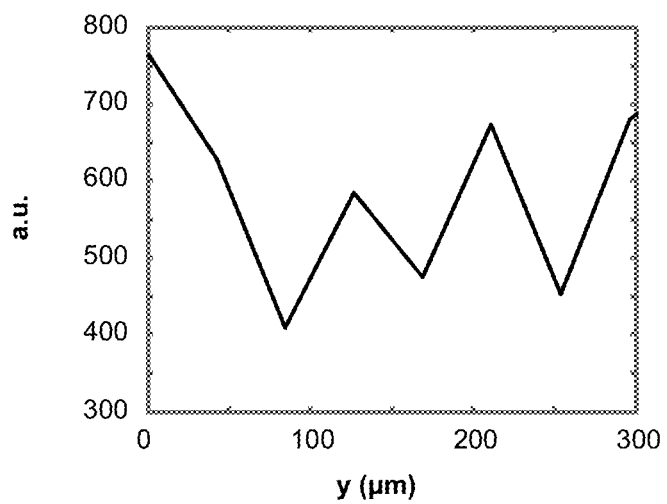

FIG. 9A is a circumferential image captured of the transparency during the image acquisition process, according to an embodiment. FIG. 9B is a zoomed-in rectangular region (denoted by line around rectangular region shown in FIG. 9A). FIG. 9B shows that the 11.3 line pairs per mm (lp/mm) (corresponding to a 88.5 µm line spacing) element (labeled as dotted rectangle) of the image is visually discernible. FIG. 9 includes intensity profiles of the 11.3 line pairs per mm (lp/mm) element in the x(c) and y(d) directions after summing the red, green, and blue (RBG) channels.

As shown in FIGS. 9A-9D, the element with 11.3 lp/mm, corresponding to a 88.5 µm line spacing, is the smallest discernible element. Based on this observation, a resolution of 89 µm is determined. This resolution is consistent with the image sensor's Nyquist sampling limit of 85 µm, considering that the pixel pitch for the sensor is 42.3 µm (600 dpi). The line visibility in the collected images and the close fit of the observed resolution to the Nyquist resolution limit suggests that the sensor pixel pitch, rather than the optical imaging scheme, was the resolution-limiting factor in our sample. In other embodiments, a rotational scanning endoscope system 14 having an image sensor having a more dense pixel pitch than 42.3 µm (600 dpi) can achieve a finer resolution.

2. Depth-of-Field

Figure 10A:
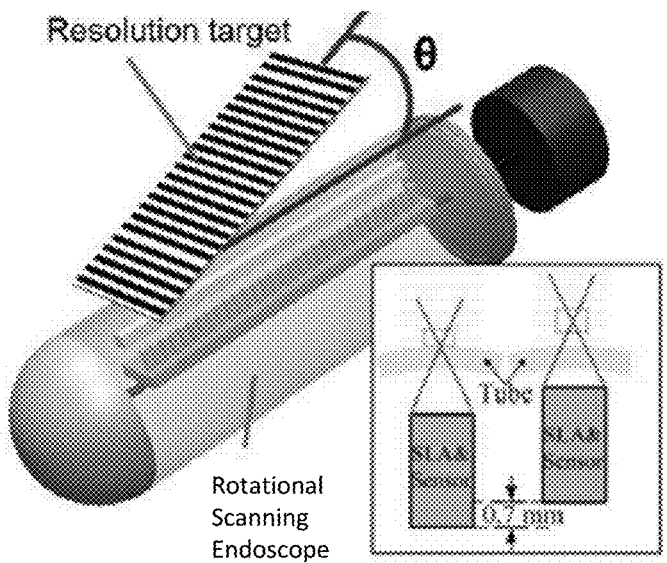
FIG. 10A is a schematic diagram of the rotational scanning endoscope system 14 for measuring depth-of-field, according to an embodiment.

The depth-of-field of the rotational scanning endoscope system 14 described with respect to FIG. 8 is characterized to demonstrate its tolerance of tissue unevenness. FIG. 10A is a schematic diagram of the rotational scanning endoscope system 14 for measuring depth-of-field, according to an embodiment. To measure the depth-of-field, the imaging module was raised by 0.7 mm to make sure that the focal plane of the lens array (e.g., SLA) was above the outer surface of the tube. A resolution target with a 5.9 -lp/mm (170-µm line spacing) line pattern was printed on a transparency film and the transparency film was attached to the outer surface of the cylindrical center portion of the tube with a tilting angle of θ=1/15 rad as shown in FIG. 10A. The illuminator was disabled and an external light source was used to provide a uniform illumination onto the target.

Figure 10B:
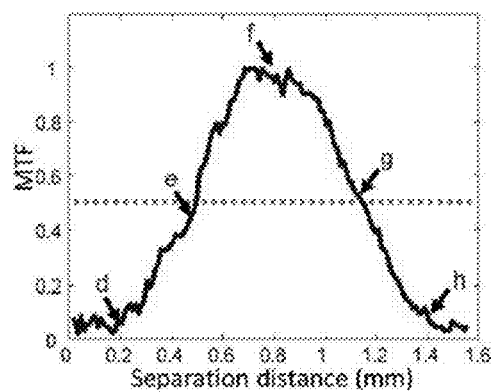
FIG. 10B is a measured modulation transfer function (MTF) of the rotational scanning endoscope system 14 corresponding to the separation distance of the line pattern, according to an embodiment.
Figure 10C:
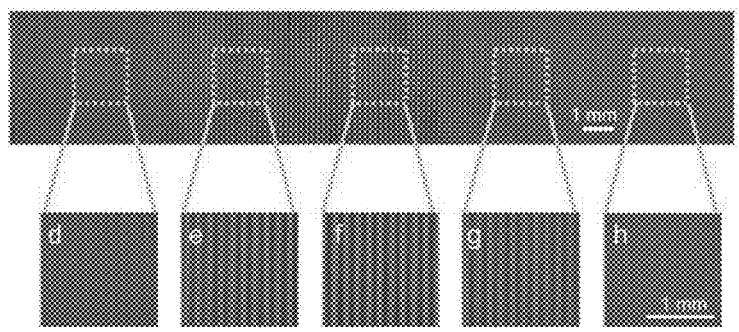
FIG. 10C is a circumferential image captured of the transparency during an image acquisition process, according to an embodiment.

After obtaining the scanned circumferential image, the modulation transfer function (MTF) at different separation distances was defined as the normalized contrast of the line pattern, and the result was plotted. FIG. 10C is a circumferential image captured of the transparency during an image acquisition process, according to an embodiment. FIG. 10C also includes zoomed-in rectangular regions d-h. FIG. 10B is a measured modulation transfer function (MTF) of the rotational scanning endoscope system 14 corresponding to the separation distance of the line pattern, according to an embodiment. The DOF was then defined as the depth range where the MTF was above 50%, which was calculated to be 0.65 mm at 5.9 lp/mm. The zoomed-in rectangular regions d-h show the line pattern at different distances below (distance of 0.2 mm at region d and distance of 0.5 mm at region e), at (distance of 0.8 mm at region f), and above (distance of 1.1 mm at region g and distance of 1.4 mm at region h) the focal plane.

3. Entire Anal Canal Imaging

Figure 13A:
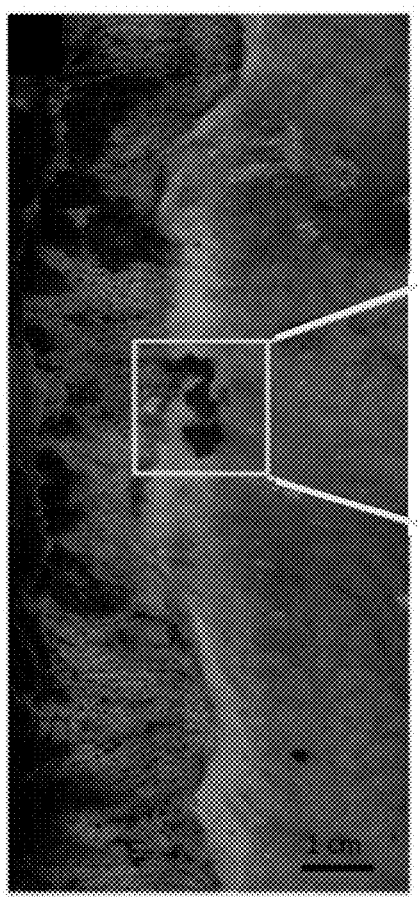
FIG. 13A is a wide field-of-view (FOV) image of the stained region captured by the rotational scanning endoscope system during the image acquisition process, according to an embodiment.
Figure 13A:
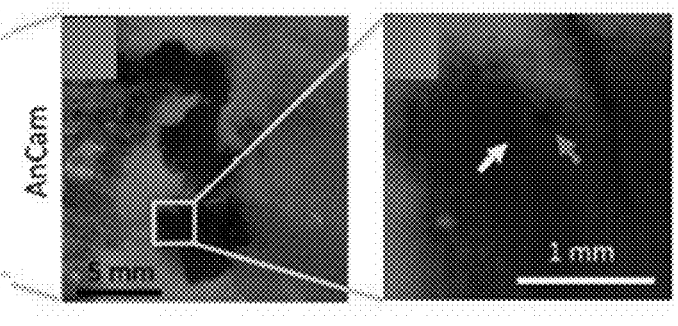
Figures 14A, 14B:
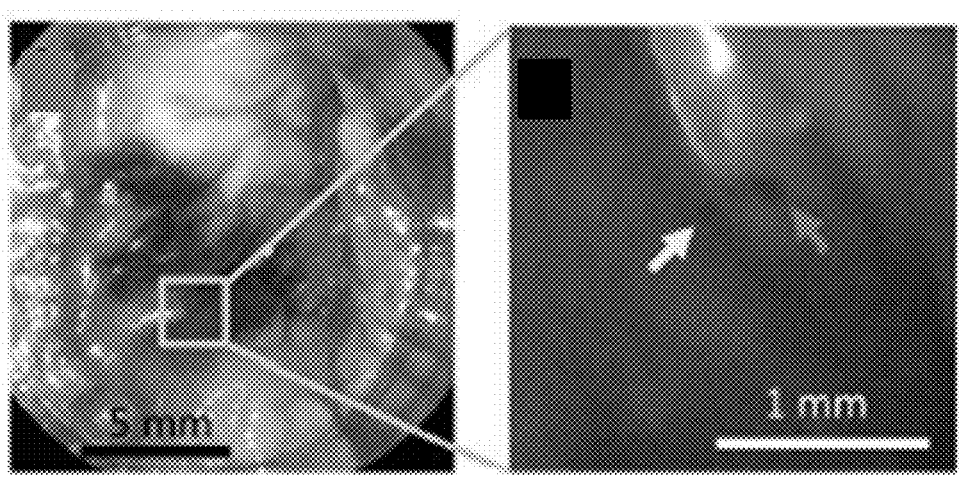
FIG. 14A is an image from a colposcope imaging process.
FIG. 14B is an image from a colposcope imaging process.

FIGS. 11, 13A, 13B, and 13C are illustrations demonstrating a rotational scanning endoscope method that captures the circumferential inner cylindrical surface of an anal canal, according to an embodiment. FIGS. 14A and 14B are images from a colposcope imaging process for comparison.

Figure 11:
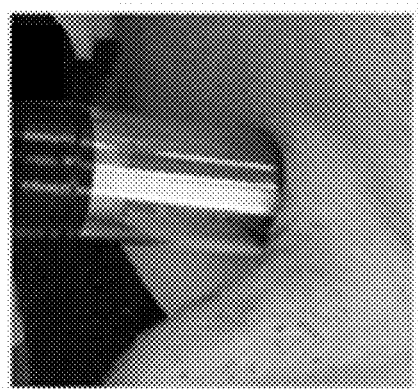
FIG. 11 is a photograph showing a rotational scanning endoscope being inserted into a live anesthetized pig, according to an embodiment.
Figure 12:
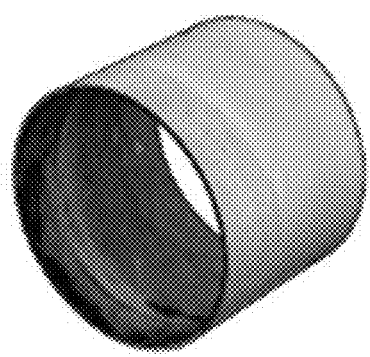
FIG. 12 is a drawing of the cylindrical surface of the entire anal canal imaged with the single scan, according to an embodiment

In the illustrated rotational scanning endoscope method, the rotational scanning endoscope system 14 described with respect to FIG. 8 was used to image the anal canal of a live anesthetized pig. After the pig was anesthetized, a small region of the anal canal was stained using a marker pen. The rotational scanning endoscope was lubricated with a small a small amount of water-based lubrication and inserting into the anus and into the anal canal. FIG. 11 is a photograph showing the rotational scanning endoscope being inserted into the anus of the live anesthetized pig, according to an embodiment. The entire cylindrical surface of the anal canal was imaged in a single scan (360 degree rotation of the imaging module). FIG. 12 is a drawing of the cylindrical surface of the entire anal canal imaged with the single scan. FIGS. 13A, 13B, and 13C are wide field-of-view (FOV) images captured by the rotational scanning endoscope system during the image acquisition process. The image in FIG. 13A has a FOV of 55 mm×120 mm. FIG. 13B is a zoomed-in image of the rectangular region indicated in FIG. 13C. FIG. 13C is a zoomed-in image of the rectangular region indicated in FIG. 13B. The stained patterns made from the marker pen are discernible in FIGS. 13B and 13C.

As a comparison, the same area of the anal canal was examined using a plastic anoscope and a standard colposcope (Olympus OCS-3) with 12× magnification, and the image was captured using an iPhone 4S camera connected to the eyepiece via a customized adaptor. FIG. 14A and FIG. 14B are images of the same stained region captured by a standard colposcope with 12× magnification. FIG. 14B is a zoomed-in image and 90° rotated image of the rectangular region indicated in FIG. 14A.

The arrows in FIG. 13C and in FIG. 14B are pointing to the same stained spots viewed under the two systems, as marked by the pen. Both the rotational scanning endoscope system 14 and the colposcope can resolve these stained spots. It is also worth noting that the colposcope images FIG. 14A and FIG. 14B have unavoidable reflections on the tissue surface due to the illumination of the light source affecting visualization of the anal mucosa. In certain embodiments, the rotational scanning endoscope system does not have these undesirable reflections.

Figure 15A:
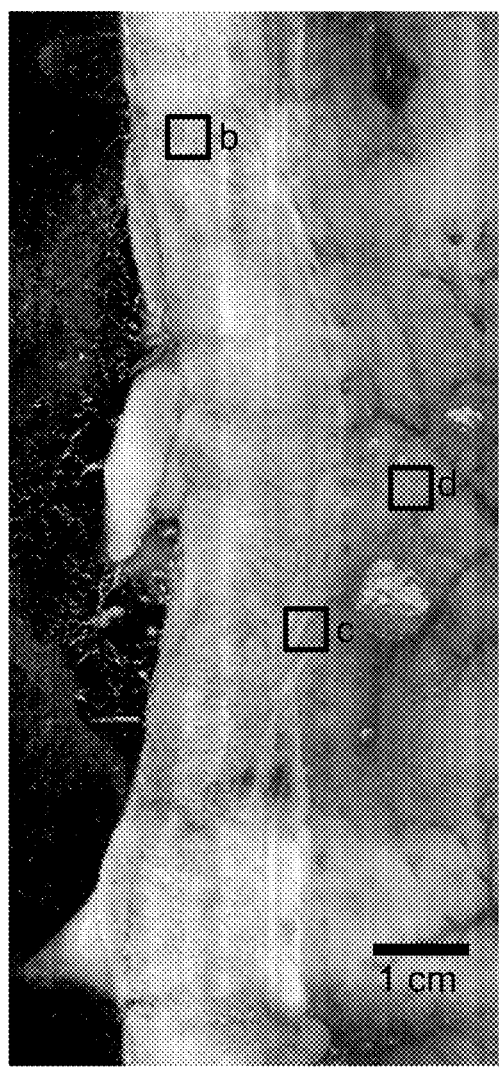
FIG. 15A is a wide field-of-view image captured by the rotational scanning endoscope system during the image acquisition process, according to an embodiment.
Figure 15B:
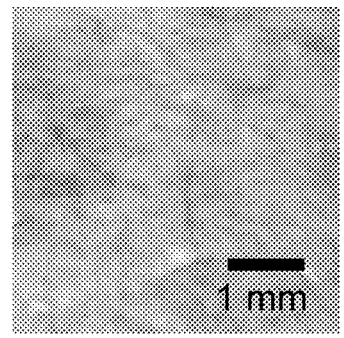
FIG. 15B is a zoomed-in image of the rectangular region "b" of the image in FIG. 15A, according to an embodiment.
Figure 15C:
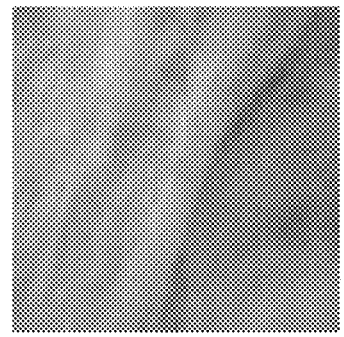
FIG. 15C is a zoomed-in image of the rectangular region "c" of the image in FIG. 15A, according to an embodiment.
Figure 15D:
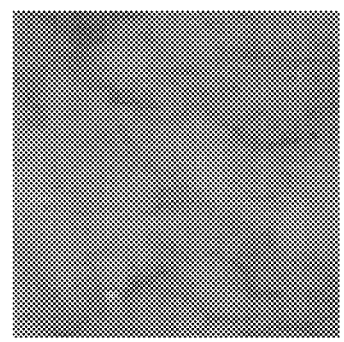
FIG. 15D is a zoomed-in image of the rectangular region "d" of the image in FIG. 15A, according to an embodiment.

FIGS. 15A-15D are wide field-of-view image of the anal canal of a live anesthetized pig captured by the rotational scanning endoscope system during the image acquisition process, according to an embodiment. FIG. 15B is a zoomed-in image of the rectangular region b indicated in FIG. 15A. FIG. 15C is a zoomed-in image of the rectangular region c indicated in FIG. 15A. FIG. 15D is a zoomed-in image of the rectangular region d indicated in FIG. 15A. Different types of tissue are observable from the images in FIGS. 15B-15D: FIG. 15B shows squamous mucosa; FIG. 15C shows dentate line; and FIG. 15D shows rectum.

III. Time-Lapsed Imaging Methods

In certain embodiments described above, the rotational scanning endoscope system can scan a full image of the circumferential surface in about 10 seconds or less. In certain aspects, this rotational scanning endoscope system can provide fast and convenient imaging, which may be useful in applications that require longitudinal monitoring such as screening for anal cancer.

Certain embodiments are directed to a time-lapsed imaging method that uses a rotational scanning endoscope system (i.e., a time-lapsed rotational scanning endoscope imaging method). This method can be used for longitudinal monitoring. Since the rotational scanning endoscope may be positioned and orientated differently during different imaging sessions (e.g., from one patient visit to the next visit) over time, this time-lapsed imaging method may realign the time-lapsed images to determine the changes in the images (e.g., potential development of anal cancer at a certain position). The aligning reference point may be, for example, a main blood vessel inside an anal canal. This time-lapsed imaging method recognizes the pattern of the reference point in the time-lapsed images and aligns the images to make the reference point appear in the same position and orientation.

Figure 16:
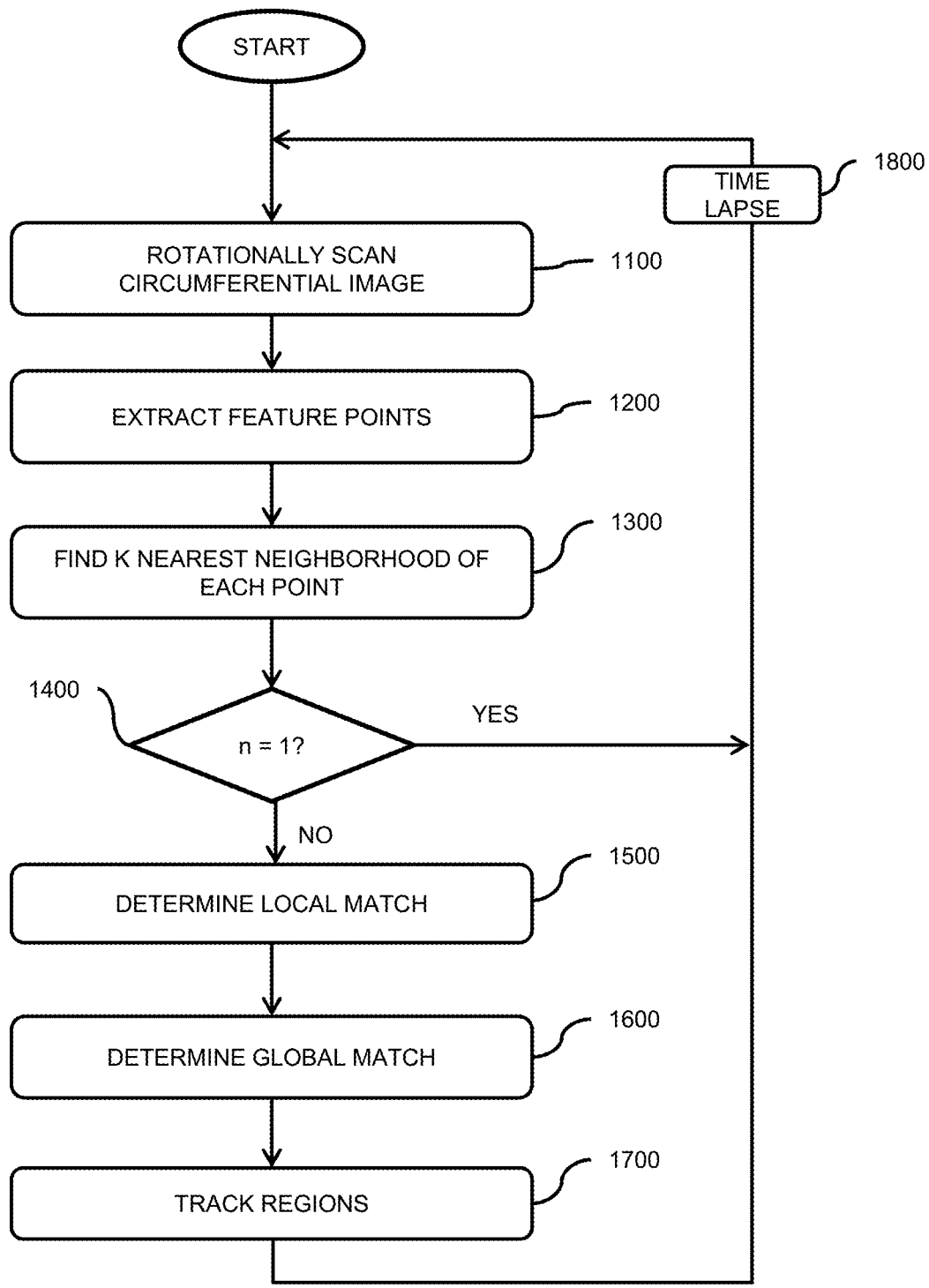
FIG. 16 is a flowchart of a time-lapsed rotational scanning endoscope imaging method, according to an embodiment.

FIG. 16 is a flowchart of a time-lapsed rotational scanning endoscope imaging method, according to an embodiment. The rotational scanning endoscope system 12 described with respect to FIG. 3 is used to generate the time-lapsed images.

At step 1100, a rotational scan of the circumferential surface outside the rotational scanning endoscope is performed. The imaging module within the substantially transparent tube is rotated about the longitudinal axis by about 360 degrees to obtain the image. Typically, the imaging module is rotated at a constant speed. During rotation, the light emitter provides illumination (e.g., RGB illumination) and a light guide channels uniform illumination to a longitudinal strip (i.e. strip parallel to direction of the longitudinal axis) along the circumferential surface. A lens array receives light issuing from the illuminated specimen and projects an image of a longitudinal strip segment onto the surface of the image sensor. At each sample time, the image sensor captures a raw image of the longitudinal segment of the specimen illuminated at that sample time. In many cases, the image sensor captures data based on three color channel illumination. The multiple raw images of longitudinal strip segments can be combined to generate the circumferential image.

At step 1200, reference points of features in the pattern in the image are extracted. For example, a blood vessel in an anal canal may be located in the circumferential image and the end points and branch points of the vessel can be extracted as the feature points.

At step 1300, the k nearest neighborhood of each point in the pattern is determined. A technique for recognizing and matching fingerprints can be found in Van Wamelena, P. B., Lig, Z., Iyengar, S. S., "A fast expected time algorithm for the 2-D point pattern matching problem. Pattern Recognition," Volume 37, Issue 8, Pages 1699-1711 (August 2004), which is hereby incorporated by reference for the details of the matching technique. Portions of this matching technique may be similar to those used in the time-lapsed rotational imaging method. At step 1400, it is determined whether it is the first image scanning (n=1) procedure. If it is the first scanning procedure performed, then the method goes to step 1800. At step 1800, a certain amount of time elapses (time lapse) before returning to step 1100 for the next imaging scanning procedure. For example, a patient may have an annual exam that has a time lapse of about one year.

If at step 1400, it is determined that it is not the first procedure performed (n=2, 3, 4, etc.), then the processor tries to determine a good local match for each reference point (step 1500). To determine a good local match, each reference point's k nearest neighborhood between the two images is compared to determine a local transformation (rotation, translation, and scaling) that makes it a good match.

At step 1600, a global match is found by using the complete point pattern and the transformation parameters from the best local match found at step 1500.

At step 1700, it is determined which regions have undergone significant changes and the regions will be tracked. For example, the regions will be stored in a database on the patient records in a computer readable medium on the computing device. In some cases, significant changes may be a sign of early anal cancer. After step 1700, the method returns to step 1100 after a certain amount of time elapses (time lapse) for the next imaging scanning procedure.

Delineation of acetowhite tissues is a critical step in standard high resolution anoscopy and requires application of acetic acid to dehydrate anal mucosa cells. Acetic acid-induced changes of the epithelial surface localize abnormal areas that require biopsy. An example of an acetowhite test can be found in B. Kumar and S. Gupta, "The acetowhite test in genital human papillomavirus infection in men: what does it add?," J. Eur. Acad. Dermatol. 15, 27-29 (2001), which is hereby incorporated by reference for the general description of this acetowhite test.

To demonstrate that the rotational scanning endoscope system can depict the dynamic changes in the anal mucosa with serial acetic acid application and of localizing acetowhite areas, the acetic acid testing was performed on a live, anesthetized pig. FIGS. 17A-17E are time-lapse wide field-of-view images of the anal canal of the live, anesthetized pig after three rounds of acetic acid staining, according to an embodiment. The rotational scanning endoscope system was used to perform time-lapse imaging of acetic acid-induced changes of the anal canal to show the dynamic changes resulting from the use of acetic acid on the epithelium as well as the reproducibility of the serial images. The time-lapse wide field-of-view images were generated by a rotational scanning endoscope system 12 described with respect to FIG. 3, according to an embodiment.

Figure 17A:
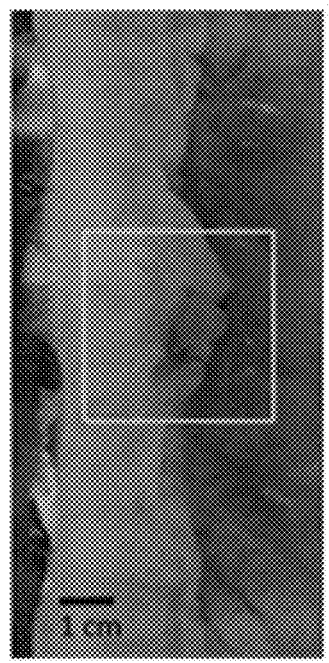
FIG. 17A is a wide FOV image of the anal canal of the live, anesthetized pig before staining, according to an embodiment.
Figure 17B:
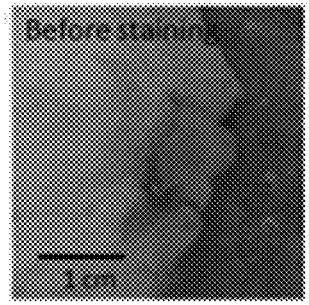
FIG. 17B is zoomed-in image of a rectangular region indicated in FIG. 17A, according to an embodiment.

First, the appearance of the anal canal was documented before acetic acid staining FIGS. 17A-17B are the wide field-of-view images of the anal before staining FIG. 17B is a zoomed-in image of the rectangular region indicated in FIG. 17A.

Figure 17C:
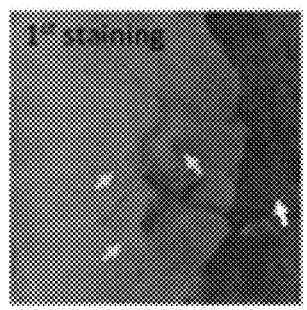
FIG. 17C is a wide FOV image of the anal canal of the live, anesthetized pig after a first round of staining, according to an embodiment.
Figure 17D:
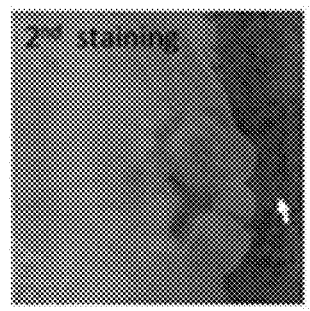
FIG. 17D is a wide FOV image of the anal canal of the live, anesthetized pig after a second round of staining, according to an embodiment.
Figure 17E:
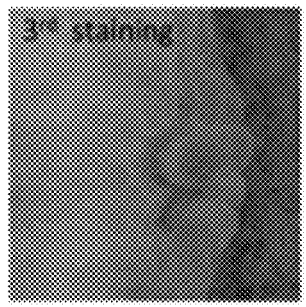
FIG. 17E is a wide FOV image of the anal canal of the live, anesthetized pig after a second round of staining, according to an embodiment.

Next, a 5% acetic acid-soaked gauze was inserted into the anal canal for 5 minutes. The gauze was removed, and a rotational scanning endoscope image was obtained. FIG. 17C is the wide field-of-view image of the anal canal after the first round of staining As shown, there was a significant whitening of the anal canal epithelium (yellow arrows) and rectum epithelium (white arrow). The application of acetic acid was repeated three times, removing the gauze, reinserted the rotational scanning endoscope image, and obtained serial time-lapse images of the anal canal. FIG. 17D the wide field-of-view image of the anal canal after the second round of staining As shown, more regions of the anal canal and rectum became whitened after this second round. FIG. 17E the wide field-of-view image of the anal canal after the third round of staining As shown, the tissue did not become further whitened. Next, the entire anal canal before application of acetic acid was compared to the post-acetic acid images. An area of interest before and after the three rounds of acetic acid staining is shown by arrows in FIGS. 17B-17E. As shown, there was a significant whitening of the anal canal epithelium (yellow arrows) and rectal epithelium (white arrow) after each of the first two stainings However, there was no further change after the third staining In each of the images in FIGS. 17B-17E, the anatomic structure of interest was reproduced and comparable. The consistency of the acquired wide field-of-view images appears to indicate that the rotational scanning endoscope can be used in longitudinal follow-up of patients with anal canal pathology.

IV. Subsystems

Figure 18:
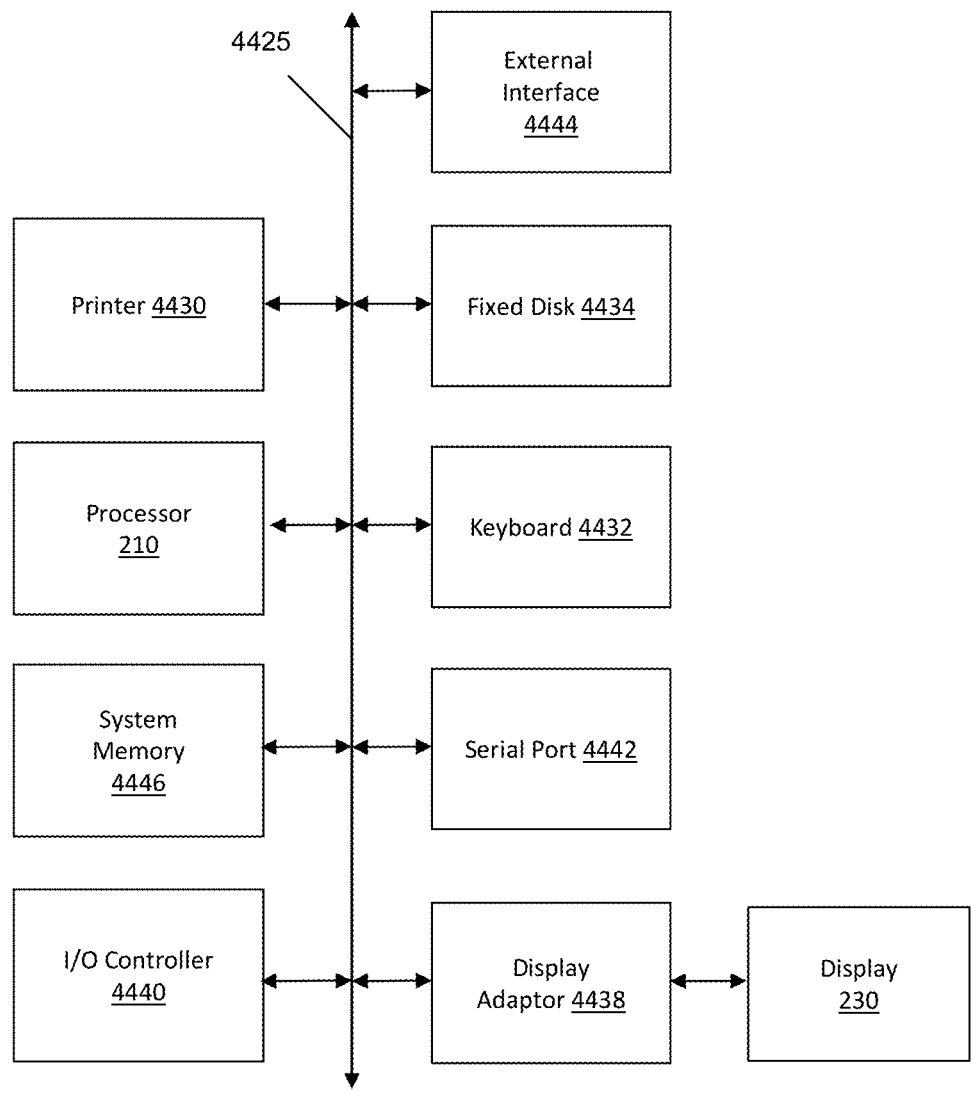
FIG. 18 is a block diagram of subsystems that may be present in certain rotational scanning endoscope systems described herein.

FIG. 18 is a block diagram of subsystems that may be present in certain rotational scanning endoscope systems described herein. For example, a rotational scanning endoscope system may include one or more processors that are part of one or more of the computing device, light emitter, image sensor, and motor.

The various components previously described in the Figures may operate using one or more of the subsystems to facilitate the functions described herein. Any of the components in the Figures may use any suitable number of subsystems to facilitate the functions described herein. Examples of such subsystems and/or components are shown in a FIG. 18. The subsystems shown in FIG. 18 are interconnected via a system bus 4425. Additional subsystems such as a printer 4430, keyboard 4432, fixed disk 4434 (or other memory comprising computer readable media), display 230, which is coupled to display adapter 4438, and others are shown. Peripherals and input/output (I/O) devices, which couple to I/O controller 4440, can be connected by any number of means known in the art, such as serial port 4442. For example, serial port 4442 or external interface 4444 can be used to connect the computing device 200 to a wide area network such as the Internet, a mouse input device, or a scanner. The interconnection via system bus 4425 allows the processor to communicate with each subsystem and to control the execution of instructions from system memory 4446 or the fixed disk 4434, as well as the exchange of information between subsystems. The system memory 4446 and/or the fixed disk 4434 may embody the CRM 220 in some cases. Any of these elements may be present in the previously described features.

In some embodiments, an output device such as the printer 4430 or display 230 of the rotational scanning endoscope system can output various forms of data. For example, the rotational scanning endoscope system can output 2D color/monochromatic images (intensity and/or phase), data associated with these images, or other data associated with analyses performed by the rotational scanning endoscope system.

Modifications, additions, or omissions may be made to any of the above-described embodiments without departing from the scope of the disclosure. Any of the embodiments described above may include more, fewer, or other features without departing from the scope of the disclosure. Additionally, the steps of the described features may be performed in any suitable order without departing from the scope of the disclosure.

It should be understood that certain features of embodiments of the disclosure described above can be implemented in the form of control logic using computer software in a modular or integrated manner. Based on the disclosure and teachings provided herein, a person of ordinary skill in the art will know and appreciate other ways and/or methods to implement certain features using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM, such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A rotational scanning endoscope:
a substantially transparent tube configured for insertion into a specimen, the tube having an outer cylindrical surface;
a motor external to the tube and configured to rotate an axial member that defines a longitudinal axis, wherein the motor rotates at a first rotating speed; and
an imaging module mounted to the axial member located within the substantially transparent tube, wherein the imaging module is configured to rotationally scan a circumferential surface outside the tube during a rotation of the axial member, wherein the imaging module includes:
an illuminator configured to provide illumination to a longitudinal segment of the specimen;
a lens array configured to project an image of an illuminated segment of the specimen to an image sensor; and
the image sensor configured to capture the image of the illuminated segment, wherein the illuminator, lens array and image sensor are co-extensive along a length of the longitudinal axis, wherein the first rotating speed of the motor is calibrated to match a frame rate of the image sensor, wherein the image sensor is located at a total conjugate distance from the outer cylindrical surface of the tube and wherein the lens array is located equidistance to the outer cylindrical surface of the tube and to the image sensor;
wherein the motor, the tube, and the axial member are co-axially aligned along the longitudinal axis and wherein the motor rotates the axial member about the longitudinal axis;
wherein the imaging module captures multiple images of illuminated segments with each image of the multiple images being captured at a sample time.

2. The rotational scanning endoscope of claim 1, wherein the lens array is an array of cylindrical lenses, wherein the lens array and the image sensor are located such that the lens array projects a 1:1 image to the image sensor.

3. The rotational scanning endoscope of claim 1, wherein the lens array is an array of SELFOC lenses.

4. The rotational scanning endoscope of claim 1, further comprising a processor for generating a circumferential image of the specimen based on the images of multiple segments of the specimen captured by the image detector at multiple sample times.

5. The rotational scanning endoscope of claim 1, wherein the illuminator comprises:
a light emitter, the light emitter being a one-dimensional array of discrete light elements; and
a light guide juxtaposed with the elongated light emitter, the light guide configured to receive light from the light emitter and provide illumination to a longitudinal segment of the specimen, the light guide being a one dimensional array of discrete light guides that corresponds to the one-dimensional array of discrete light elements, wherein each discrete light guide corresponds to a discrete light element in one-to-one correspondence;
wherein the illuminator has a length that extends along a majority of the length of the transparent tube.

6. The rotational scanning endoscope of claim 5, wherein the light emitter provides RGB illumination.

7. The rotational scanning endoscope of claim 5, wherein each discrete light elements comprises three LEDs including a red light source, a blue light source, and a green light source.

8. The rotational scanning endoscope of claim 1, wherein the motor further comprises a gear between the motor and the axial member.

9. The rotational scanning endoscope of claim 1, further comprising an adapter comprising a distal end configured to engage with the tube and a proximal end configured to receive the motor and the axial member.

10. The rotational scanning endoscope of claim 1, wherein the tube comprises a rounded distal end for insertion into the specimen and a proximal end with an opening for receiving the adapter of the motor.

11. The rotational scanning endoscope of claim 1, wherein the specimen is an anal canal.

12. The rotational scanning endoscope of claim 4, wherein the circumferential image of the specimen is of a cylindrical surface.

13. A rotational scanning endoscope system:
a tube configured for insertion into a specimen, the tube having an outer cylindrical surface;
a motor external to the tube and configured to rotate an axial member that defines a longitudinal axis, wherein the motor rotates at a first rotating speed;
an imaging module mounted to the axial member located within the tube, wherein the imaging module is configured to rotationally scan a surface outside the tube during rotation of the axial member, wherein the imaging module includes:
an illuminator configured to provide illumination to a longitudinal segment of the specimen;
a lens array configured to project an image of an illuminated segment of the specimen to an image sensor; and
the image sensor configured to capture the image of the illuminated segment, wherein the illuminator, lens array and image sensor are co-extensive along a length of the longitudinal axis, wherein the first rotating speed of the motor is calibrated to match a frame rate of the image sensor, wherein the image sensor is located at a total conjugate distance from the outer cylindrical surface of the tube and wherein the lens array is located equidistance to the outer cylindrical surface of the tube and to the image sensor;
wherein the motor, the tube, and the axial member are co-axially aligned along the longitudinal axis and wherein the motor rotates the axial member about the longitudinal axis; and
one or more processors configured to generate an image of the specimen based on the rotational scan.

14. The rotational scanning endoscope system of claim 13, wherein the lens array comprises an array of SELFOC lenses (SLA) configured to project an image of the illuminated segment to the image sensor.

15. The rotational scanning endoscope system of claim 14, wherein the SLA and the image sensor are located such that the SLA projects a 1:1 image to the image sensor.

16. The rotational scanning endoscope system of claim 14, wherein processor generates the image of the specimen based on the images of multiple segments of the specimen captured by the image detector at multiple sample times.

17. The rotational scanning endoscope system of claim 14, wherein the illuminator comprises:
   a light emitter, the light emitter being a one-dimensional array of discrete light elements; and
   a light guide juxtaposed with the elongated light emitter, the light guide configured to receive light from the light emitter and provide illumination to a longitudinal segment of the specimen, the light guide being a one dimensional array of discrete light guides that corresponds to the one-dimensional array of discrete light elements, wherein each discrete light guide corresponds to a discrete light element in one-to-one correspondence;
   wherein the illuminator has a length that extends along a majority of the length of the transparent tube.

18. The rotational scanning endoscope system of claim 17, wherein the light emitter provides RGB illumination.

19. The rotational scanning endoscope system of claim 14, wherein the illuminator comprises an RGB light pipe.

20. The rotational scanning endoscope system of claim 14, wherein the tube comprises a rounded distal end for insertion into the specimen and proximal end with an opening for receiving an adapter of the motor assembly.

* * * * *